United States Patent [19]

Suzuki et al.

[11] Patent Number: 5,646,283

[45] Date of Patent: Jul. 8, 1997

[54] TETRACYCLIC COMPOUND

[75] Inventors: Fumio Suzuki; Yoshisuke Nakasato; Hiroshi Tsumuki; Soichiro Sato; Tadafumi Tamura; Hiroshi Nakajima, all of Shizuoka, Japan

[73] Assignee: Kyowa Hakko Kogyo Co., Ltd., Tokyo, Japan

[21] Appl. No.: 436,370

[22] PCT Filed: Sep. 28, 1994

[86] PCT No.: PCT/JP94/01591

§ 371 Date: May 22, 1995

§ 102(e) Date: May 22, 1995

[87] PCT Pub. No.: WO95/09153

PCT Pub. Date: Apr. 6, 1995

[30] Foreign Application Priority Data

Sep. 28, 1993 [JP] Japan .................. 5-241360

[51] Int. Cl.[6] .................. C07D 221/18
[52] U.S. Cl. .................. 546/61
[58] Field of Search .................. 546/61; 514/284

[56] References Cited

U.S. PATENT DOCUMENTS 4,918,077  4/1990  Behrens .................. 514/284

FOREIGN PATENT DOCUMENTS 0601191  6/1994  European Pat. Off. .
233661   9/1990  Japan .
WO92/00739  1/1992  WIPO .
06640   3/1995  WIPO .

OTHER PUBLICATIONS

Huisgen et al., Liebigs Ann. Chem., No. 610 (Jun. 1957) 57–66.

*Primary Examiner*—C. Warren Ivy
*Assistant Examiner*—Garth M. Dahlen
*Attorney, Agent, or Firm*—Fitzpatrick, Cella, Harper & Scinto

[57] ABSTRACT

This invention relates to a novel tetracyclic compound represented by formula (I):

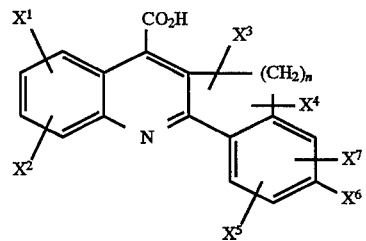

or its pharmacologically-acceptable salt.

The compound of this invention has strong immunosuppressive activity, and is useful as an immunosuppressive agent and as an agent for treating autoimmune disease.

5 Claims, 2 Drawing Sheets

TETRACYCLIC COMPOUND

This application is a 371 of PCT/JP94/01591 filed Sep. 28, 1994.

TECHNICAL FIELD

This invention relates to a novel tetracyclic compound which is useful as an immunosuppressive agent and as an agent for treating autoimmune disease.

1. Background Art

Japanese Laid-Open Patent Application No. Heisei 2-233661 discloses that a compound represented by formula (A)

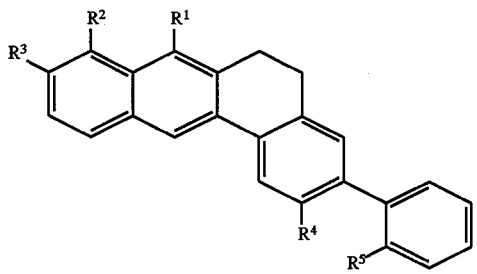

(wherein $R^1$ represents $CO_2H$, or the like, each of $R^2$ and $R^3$ independently represents H, F, or the like, and each of $R^4$ and $R^5$ independently represents H or the like) is effective as a cancer chemotherapeutant. Furthermore, an usage of the compound as an immunosuppressive agent is disclosed in WO92/00739.

A compound represented by the formula

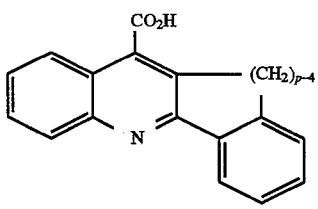

(wherein p is an integer of 5 to 8) is disclosed, but its pharmacological activity is unknown [Liebigs Ann. Chem., 610, 57 (1957)].

2. Disclosure of the Invention

An object of this invention is to provide a novel tetracyclic compound which is useful as an immunosuppressive agent and as an agent for treating autoimmune disease.

This invention provides a novel tetracyclic compound represented by formula (I) [hereinafter referred to as "compound (I)",

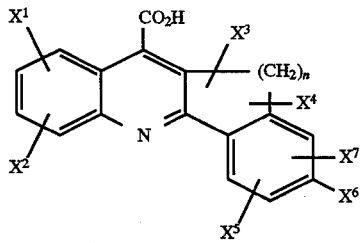

or its pharmacologically acceptable salt, (wherein $X^1$ and $X^2$ are the same or different and each represents hydrogen, a lower alkyl, halogen, nitro, hydroxy or a lower alkoxy, $X^3$ and $X^4$ are the same or different and each represents hydrogen or a lower alkyl, $X^5$ and $X^7$ are the same or different and each represents hydrogen, a lower alkyl, halogen, hydroxy or a lower alkoxy, $X^6$ represents a substituted or unsubstituted aryl, a substituted or unsubstituted aromatic heterocyclic group, cycloakyl, bicycloalkyl or tricycloalkyl, and n is an integer of 1 to 4;

provided that when n is 2, $X^6$ represents a substituted aryl, a substituted or unsubstituted aromatic heterocyclic group, cycloalkyl, bicycloalkyl or tricycloalkyl, or $X^6$ represents an unsubstituted aryl, and at least one of $X^5$ and $X^7$ represents a substituent mentioned above other than hydrogen;

and provided that when $X^1$, $X^2$ and $X^6$ are represented by formula (II),

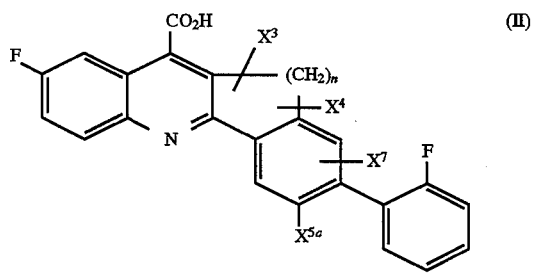

$X^{5a}$ represents a lower alkyl, halogen or a lower alkoxy, and $X^3$, $X^4$, $X^7$ and n are the same as defined above.)

In the definition of each group of formula (I), a lower alkyl and an alkyl moiety of a lower alkoxy include straight or branched alkyl group having 1 to 6 carbon atoms such as methyl, ethyl, propyl, isopropyl, butyl, isobutyl, sec-butyl, tert-butyl, pentyl, neopentyl and hexyl. Examples of the halogen atom include fluorine, chlorine, bromine and iodine. Examples of cycloalkyl include cycloalkyl groups having from 3 to 8 carbon atoms such as cyclopropyl, cyclopentyl, cyclohexyl and cyclooctyl. Examples of bicycloalkyl include bicycloalkyl group having 6 to 12 carbon atoms such as bicyclohexyl, bicyclooctyl and bicylododecyl. Examples of tricycloalkyl include tricycloalkyl groups having from 8 to 12 carbon atoms such as tricyclooctyl, tricyclononyl, tricyclodecyl and tricyclododecyl. Examples of aryl include phenyl and naphthyl. Examples of the aromatic heterocyclic group include pyridyl, thienyl, furyl, pyrazolyl, oxazolyl and imidazolyl. Substituted aryl and the substituted aromatic heterocyclic ring have 1 to 3 of the same or different substituents such as lower alkyl, trifluoromethyl, halogen, nitro, hydroxy and a lower alkoxy. Lower alkyl, halogen and lower alkoxy are the same as defined above.

The pharmacologically-acceptable salt of compound (I) includes an acid-addition salt, a metal salt, an ammonium salt, an organic-amine-addition salt and an amino-acid addition salt.

Examples of the pharmacologically acceptable acid addition salt of compound (I) include salts of inorganic acids such as hydrochloric acid, sulfuric acid and phosphoric acid; salts of organic acids such as acetic acid, maleic acid, fumaric acid, tartaric acid and citric acid. Examples of the pharmacologically acceptable metal salts include alkali metal salts such as sodium salt and potassium salt, alkaline-earth metal salts such as magnesium salt and calcium salt, aluminum salts and zinc salts. Examples of the pharmacologically acceptable ammonium salts include salts of ammonium and tetramethylammonium. Examples of the pharmacologically acceptable organic-amine-addition salt include addition salts with morpholine and piperidine, and examples of the pharmacologically-acceptable amino-acid addition salt include addition salts of lysine, glycine and phenylalanine.

A process for producing the compound of this invention is described below.

Process 1:
Compound (I-a), that is, Compound (I) in which $X^3$ and $X^4$ are both hydrogens can be obtained by the following reaction process:

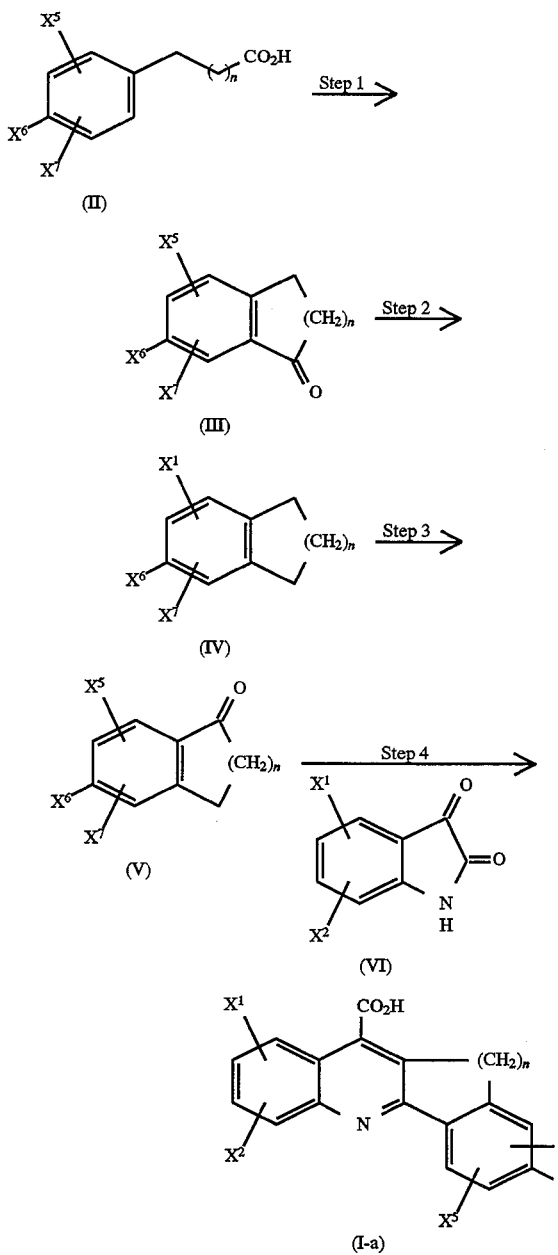

(wherein $X^1$, $X^2$, $X^5$, $X^6$, $X^7$ and n are the same as defined above.)

Step 1:
Compound (III) can be obtained by treating compound (II) usually at 50° to 120° C. for 1 to 6 hours in the absence of a solvent and in the presence of a dehydrating agent.

Examples of the dehydrating agent include polyphosphoric acid, methanesulfonic acid and sulfuric acid.

Step 2:
Compound (IV) can be obtained by reacting compound (III) with 2 to 3 equivalents of triethylsilane in trifluoroacetic acid usually at room temperature to 70° C. for 5 minutes to 6 hours.

In another method of Step 2, compound (IV) can be obtained by reacting compound (III) with 1 equivalent of hydrazine hydrate in a solvent such as diethylene glycol and triethylene glycol in the presence of potassium hydroxide at 120° C. for 2 hours and then reacting at 180° C. to 210° C. for 2 to 5 hours.

In another method of Step 2, compound (III) is reacted with 1 equivalent of a dithiol such as ethanedithiol and propanedithiol in a solvent such as dichloromethane in the presence of a trifluoroboron ether complex usually at room temperature for 2 to 48 hours. Then compound (IV) can be obtained by refluxing the reaction mixture in a solvent such as methanol and ethanol in the presence of a catalyst such as Raney nickel at room temperature or heating.

Step 3:
Compound (V) can be obtained by reacting compound (IV) with 1 to 4 equivalents of chromic acid in a mixed solvent of acetic acid and propionic acid usually at 0° C. to room temperature for 1 to 6 hours.

Step 4:
Compound (I-a) can be obtained by reacting compound (V) with 1 equivalent of compound (VI) (made by Aldrich Chemical Company Inc.) in a mixed solvent of ethanol and water under alkaline conditions such as with potassium hydroxide and sodium hydroxide usually at room temperature to 100° C. for 12 to 120 hours.

In another method of Step 4, compound (V) is reacted with 1 equivalent of compound (VI) in a solvent such as methanol and ethanol in the presence of 1 equivalent of amine such as diethylamine and diisopropylamine usually at room temperature for 12 to 48 hours. Then compound (I-a) can be obtained by heat-refluxing the reaction mixture in tetrahydrofuran-conc. hydrochloric acid for 12 to 48 hours.

The material compound (II) can be obtained by the following reaction process:

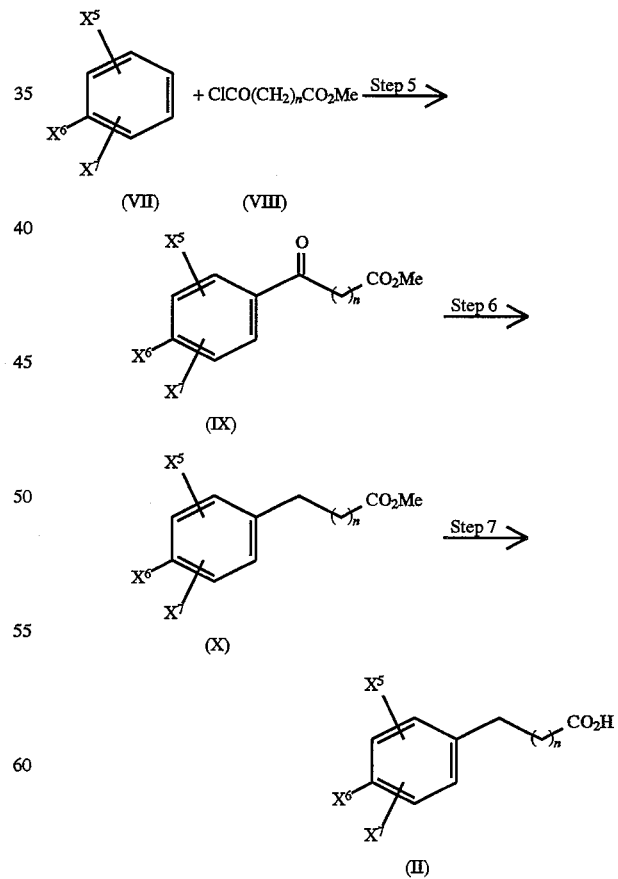

(wherein $X^5$, $X^6$, $X^7$ and n are the same as defined above, and Me represents methyl.)

Step 5:

Compound (IX) can be obtained by reacting compound (VII) (made by Aldrich Chemical Company Inc) with 1 equivalent of compound (VIII) (made by Aldrich Chemical Company Inc) in a solvent which is inert to the reaction such as dichloromethane and dichloroethane in the presence of 2 equivalents of Lewis acid such as aluminum trichloride usually at 0° C. to room temperature for 1 to 12 hours.

Step 6:

Compound (X) can be obtained from compound (IX) in almost the same manner as used in Step 2.

Step 7:

Compound (II) can be obtained by reacting compound (X) in a dioxane-water mixed solvent under alkaline conditions such as with potassium hydroxide and sodium hydroxide usually at room temperature to 100° C. for 1 to 12 hours.

In another method, compound (II-a), that is compound (II) in which n is 2 or 3, can be also obtained by the following reaction process:

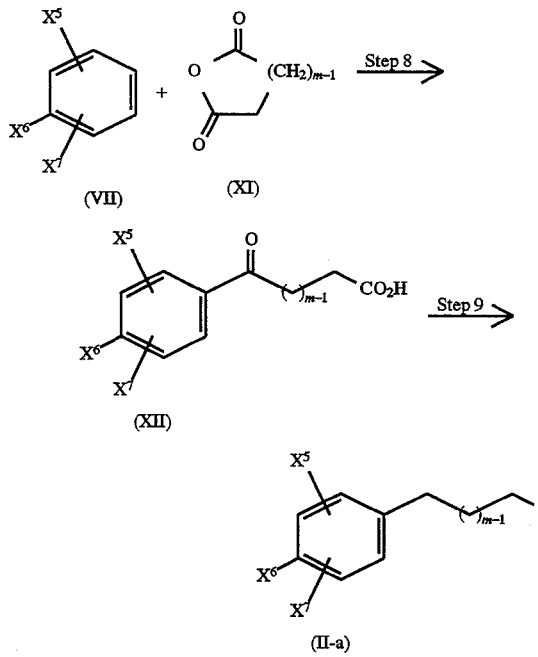

(wherein $X^5$, $X^6$ and $X^7$ are the same as defined above, and m is 2 or 3.)

Step 8:

Compound (XII) can be obtained from compound (VII) and 1 equivalent of compound (XI) (made by Aldrich Chemical Company Inc.) in almost the same manner as used in Step 5.

Step 9:

Compound (II-a) can be obtained from compound (XII) in almost the same manner as used in Step 2.

Compound (V), which is an intermediate, can be also obtained by the following reaction process:

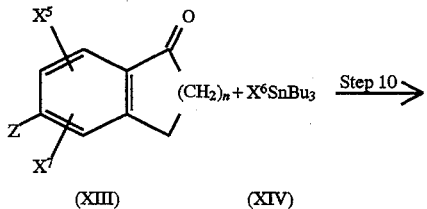

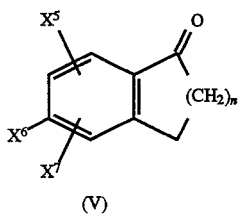

(wherein $X^5$, $X^6$, $X^7$ and n are the same as defined above, Bu represents butyl, and Z represents bromine, iodine or trifluorosulfonyloxy.)

Step 10:

Compound (V) can be obtained by reacting compound (XIII) with 1 to 2 equivalents of compound (XIV) in a solvent such as dimethylformamide, tetrahydrofuran and dioxane in the presence of a catalytic amount of a palladium complex usually at 60° to 120° C. for 1 to 12 hours. A salt such as lithium chloride and an oxidizing agent such as silver oxide may be added, if necessary. Compound (XIII) can be obtained by a known method [J. Org. Chem., 27, 70 (1962) or Tetrahedron Lett., 33, 5499 (1992)] or by similar method to the known method. Further, compound (XIV) can be obtained by a known method [Angew. Chem. Int. Ed. Engl., 25, 508 (1986)] or by similar method to the known method.

In another method, compound (V) can be also obtained by the following reaction process:

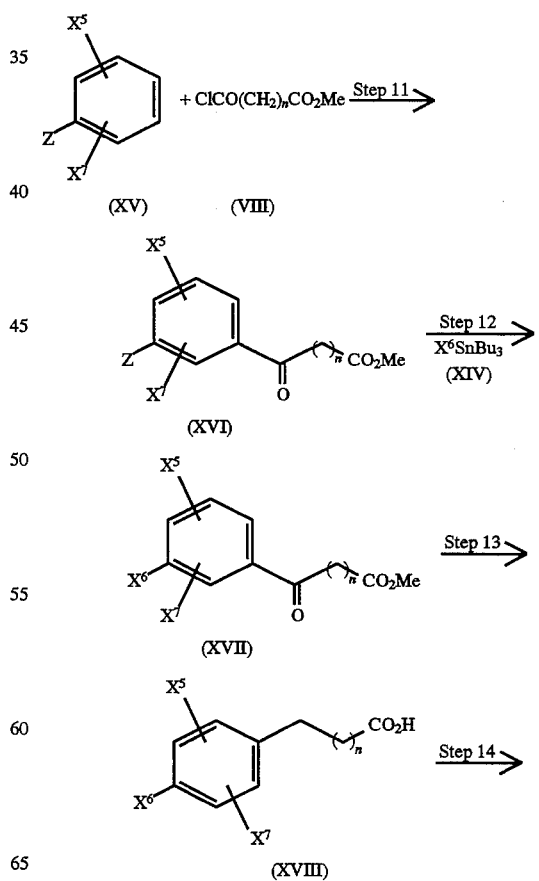

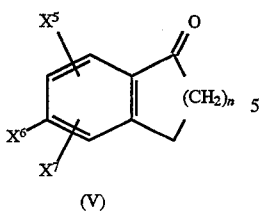

(wherein $X^5$, $X^6$, $X^7$, n, Me, Bu and Z are the same as defined above.)

Step 11:

Compound (XVI) can be obtained from compound (XV) (made by Aldrich Chemical Company Inc.) and compound (VIII) in almost the same manner as used in Step 5.

Step 12:

Compound (XVII) can be obtained from compound (XVI) and compound (XIV) in almost the same manner as used in Step 10.

Step 13:

Compound (XVIII) can be obtained from compound (XVII) in almost the same manner as used in Step 2.

Step 14:

Compound (V) can be obtained from compound (XVIII) in almost the same manner as used in Step 1.

Compound (V) can be also obtained by the following reaction process,

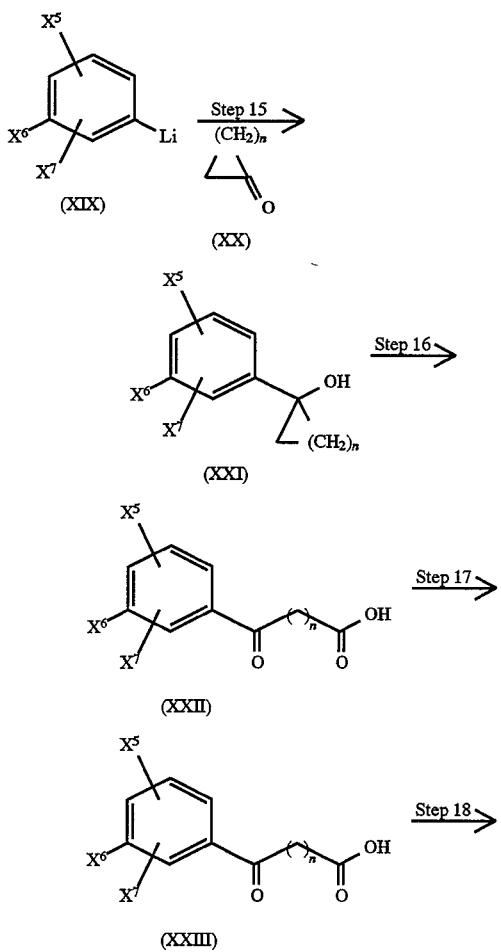

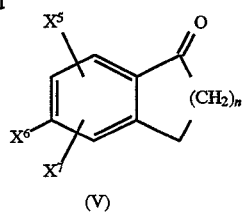

(wherein $X^5$, $X^6$, $X^7$ and n are as defined above.)

Step 15:

Compound (XXI) can be obtained by reacting compound (XIX) with 1 equivalent of compound (XX) (made by Tokyo Kasei Co. Ltd.) in a solvent such as tetrahydrofuran and ether usually at −78° to −20° C. for 5 minutes to 1 hour. Compound (XIX) can be synthesized by a known method [Organolithium Method Academic Press, (1988)] or by similar method to the known method.

Step 16:

Compound (XXII) can be obtained by reacting compound (XXI) with 3 to 10 equivalents of chromic anhydride in a solvent such as acetic acid at room temperature to 40° C. for 30 minutes to 6 hours.

Step 17:

Compound (XXIII) can be obtained from compound (XXII) in the same manner as used in Step 2.

Step 18:

Compound (V) can be obtained from compound (XXIII) in the same manner as used in Step 1.

Compound (I) in which $X^3$ and/or $X^4$ are lower alkyl groups can be obtained by the following processes 2 to 4:

Process 2:

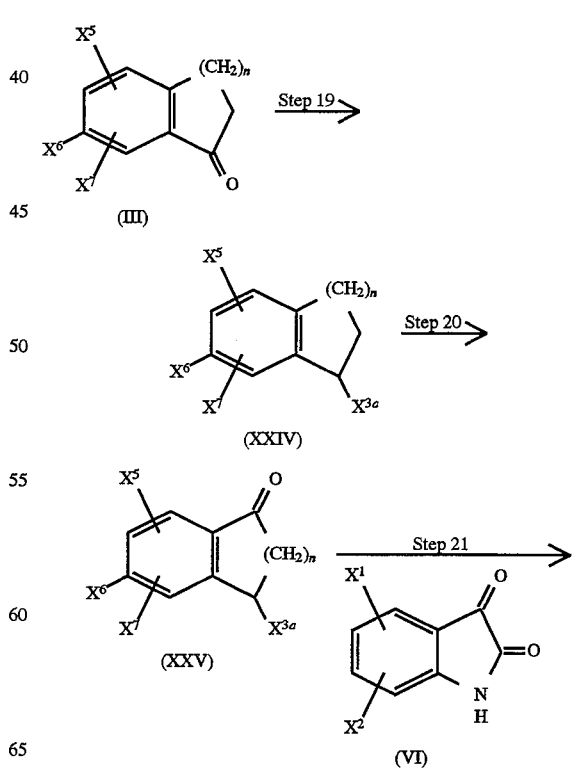

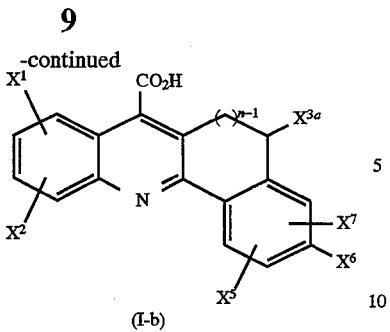

(I-b)

(wherein $X^1$, $X^2$, $X^5$, $X^6$, $X^7$ and n are the same as defined above, and $X^{3a}$ is a lower alkyl in the definition for $X^3$.)

Step 19:

Compound (III) is reacted with 1 equivalent of an alkylphosphonium salt in a solvent such as tetrahydrofuran, dioxane, dimethylformamide and dimethyl sulfoxide in the presence of a base usually at 0° to 120° C. for 5 minutes to 12 hours. Then Compound (XXIV) can be obtained by subjecting the reaction mixture to the catalytic hydrogen reduction in a solvent such as methanol, ethanol and acetic acid using a catalyst such as palladium/carbon and platinum dioxide usually at 0° to 100° C. for 5 minutes to 12 hours.

Examples of the base include n-butyllithium, potassium tert-butoxide, sodium hydride, sodium hydroxide, potassium carbonate and triethylamine.

In another method of Step 19, compound (III) is reacted with 1 to 5 equivalents of a Grignard reagent in a solvent such as ether, tetrahydrofuran and dioxane usually at –30° to 100° C. for 5 minutes to 12 hours. Then the mixture is reacted with 1 to 2 equivalents of triethylsilane in trifluoroacetic acid usually at room temperature to 70° C. for 5 minutes to 6 hours.

Step 20:

Compound (XXV) can be obtained from compound (XXIV) in almost the same manner as used in Step 3.

Step 21:

Compound (I-b) can be obtained from compound (XXV) and compound (VI) in almost the same manner as used in Step 4.

Process 3:

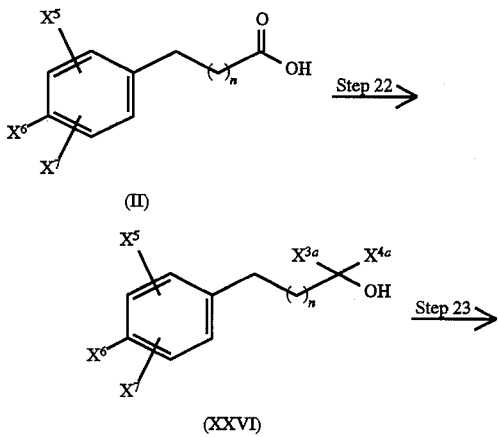

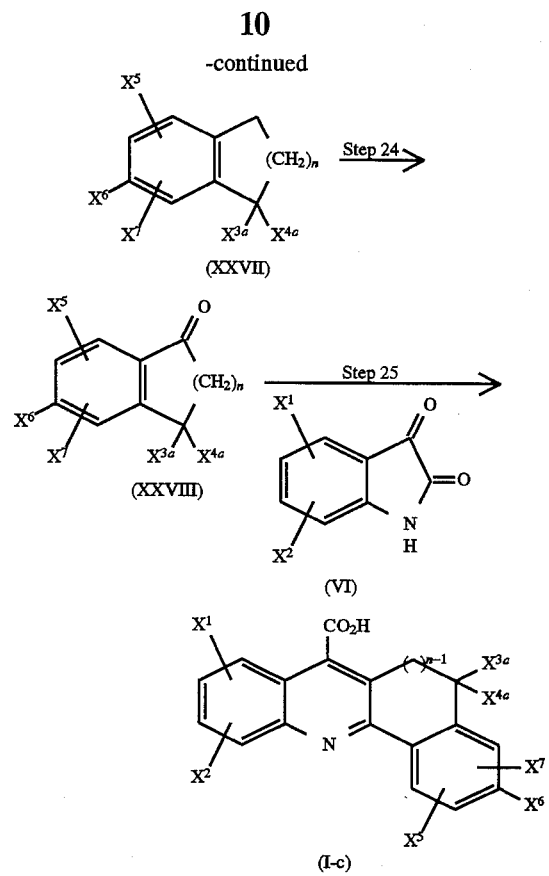

(wherein $X^1$, $X^2$, $X^{3a}$, $X^5$, $X^6$, $X^7$ and n are the same as defined above, and $X^{4a}$ is lower alkyl in the definition of $X^4$.)

Step 22:

Compound (XXVI) can be obtained by reacting compound (II) with 2 to 10 equivalents of a Grignard reagent in a solvent such as ether, tetrahydrofuran and dioxane usually at –30° to 100° C. for 5 minutes to 12 hours.

Step 23:

Compound (XXVII) can be obtained by treating compound (XXVI) in a solvent which is inert to the reaction such as dichloromethane and dichloroethane in the presence of Lewis acid such as aluminum trichloride usually at 0° C. to room temperature for 1 to 12 hours.

Step 24:

Compound (XXVIII) can be obtained from compound (XXVII) in almost the same manner as used in Step 3.

Step 25:

Compound (I-c) can be obtained from compounds (XXVIII) and compound (VI) in almost the same manner as used in Step 4.

Process 4:

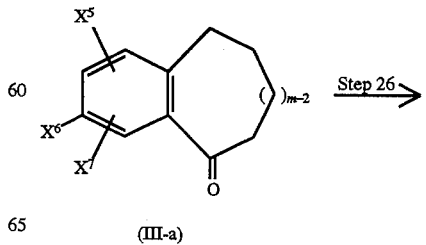

(III-a)

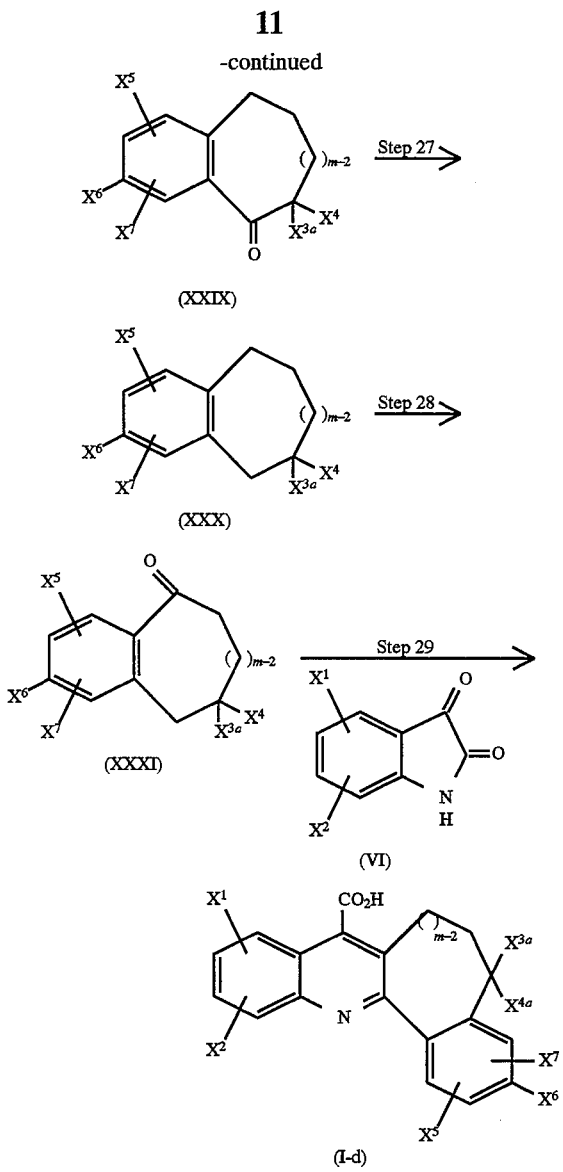

(wherein $X^1$, $X^2$, $X^{3a}$, $X^4$, $X^5$, $X^6$, $X^7$ and m are the same as defined above.)

Step 26:

Compound (XXIX) can be obtained by reacting compound (III-a), that is, compound (III) in which n is 2 or 3, with an alkyl halide such as methyl iodide and ethyl iodide in a solvent such as tetrahydrofuran, dioxane, dimethylformamide and dimethyl sulfoxide in the presence of a base at 0° to 120° C. for 5 minutes to 12 hours.

Examples of the base include sodium hydride, potassium tert-butoxide, sodium hydroxide and potassium carbonate. A phase-transfer catalyst may be added, if necessary, examples thereof being quaternary ammonium halides such as tetrabutylammonium bromide and crown ethers such as 18-crown-6.

In another method of Step 26, compound (III-a) is reacted with a secondary amine such as pyrrolidine and piperazine in a solvent such as benzene and toluene in the presence of p-toluene sulfonic acid usually under refluxing for 1 to 12 hours. Then compound (XXIX) can be obtained by reacting the reaction mixture with an alkyl halide such as methyl iodide and ethyl iodide in a solvent such as dioxane and dimethylformamide usually at room temperature to 100° C. for 5 minutes to 12 hours.

Step 27:

Compound (XXX) can be obtained from compound (XXIX) in almost the same manner as used in Step 2.

Step 28:

Compound (XXXI) can be obtained from compound (XXX) in almost the same manner as used in Step 3.

Step 29:

Compound (I-d) can be obtained from compound (XXXI) and compound (VI) in almost the same manner as used in Step 4.

The intermediates and the final compounds in the above-mentioned processes can be isolated and purified by the methods conventionally used in the organic synthetic chemistry such as filtration, extraction, washing, drying, concentration, recrystallization and various types of chromatography. The intermediates can be also subjected to the subsequent reaction without special purification.

When the salt of compound (I) is required and compound (I) is obtained in the form of the salt, it may be purified as such. When compound (I) is obtained in the free form, it may be dissolved or suspended in a suitable solvent and formed into a salt with the addition of an acid or a base.

Compound (I) and its pharmacologically-acceptable salt sometimes exists in the form of an adduct with water or various solvents. This adduct is also included in this invention.

Specific examples of compound (I) are shown in Table 1.

TABLE 1

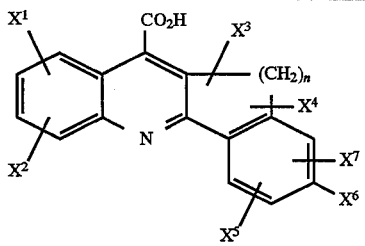

| Compound No. | n | $X^1$ | $X^2$ | $X^3$ | $X^4$ | $X^5$ | $X^6$ | $X^7$ |
|---|---|---|---|---|---|---|---|---|
| 1 | 2 | 9-F | H | H | H | H | ⟨benzene ring⟩-F | H |

TABLE 1-continued
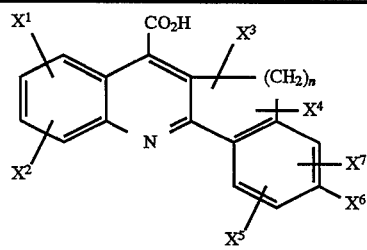
| Compound No. | n | $X^1$ | $X^2$ | $X^3$ | $X^4$ | $X^5$ | $X^6$ | $X^7$ |
|---|---|---|---|---|---|---|---|---|
| 2 | 2 | 9-F | H | H | H | H | 2,4-difluorophenyl | H |
| 3 | 2 | 9-F | H | H | H | H | 2,6-difluorophenyl | H |
| 4 | 2 | 9-F | H | H | H | H | 2-thienyl | H |
| 5 | 2 | 9-F | H | H | H | H | 2-pyridyl | H |
| 6 | 2 | 9-F | H | H | H | H | 3-pyridyl | H |
| 7 | 2 | 9-F | H | H | H | H | 4-pyridyl | H |
| 8 | 2 | 9-F | H | H | H | H | cyclohexyl | H |
| 9 | 2 | 9-OEt | H | Me | H | H | 2-fluorophenyl | H |
| 10 | 2 | 9-OEt | H | 5-Me | 5-Me | H | 2-fluorophenyl | H |
| 11 | 3 | 10-F | H | H | H | H | 2-methylphenyl | H |

TABLE 1-continued
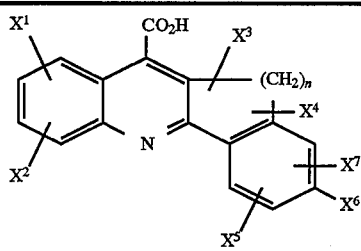
| Compound No. | n | X¹ | X² | X³ | X⁴ | X⁵ | X⁶ | X⁷ |
|---|---|---|---|---|---|---|---|---|
| 12 | 3 | 10-F | H | H | H | H | 2-CF₃-phenyl | H |
| 13 | 3 | 10-F | H | H | H | 2-F | 2-F-phenyl | H |
| 14 | 3 | 10-Me | H | H | H | H | 2-F-phenyl | H |
| 15 | 4 | 11-F | H | H | H | H | phenyl | H |
| 16 | 2 | 9-F | H | H | H | 2-F | phenyl | H |
| 17 | 2 | 9-F | H | H | H | 2-F | 2-F-phenyl | H |
| 18 | 2 | 9-F | H | H | H | 2-F | 4-F-phenyl | H |
| 19 | 3 | 10-F | H | H | H | H | 4-F-phenyl | H |
| 20 | 3 | 10-F | H | H | H | H | 3-F-phenyl | H |
| 21 | 3 | 10-F | H | H | H | H | 2,4-diF-phenyl | H |

TABLE 1-continued
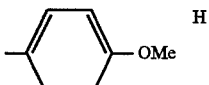
| Compound No. | n | X¹ | X² | X³ | X⁴ | X⁵ | X⁶ | X⁷ |
|---|---|---|---|---|---|---|---|---|
| 22 | 3 | 10-F | H | H | H | H | 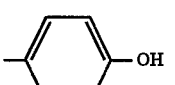 —OMe | H |
| 23 | 3 | 10-F | H | H | H | H | 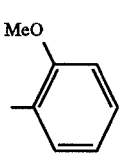 —OH | H |
| 24 | 3 | 10-F | H | H | H | H | MeO 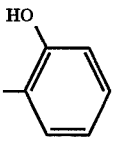 | H |
| 25 | 3 | 10-F | H | H | H | H | HO 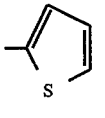 | H |
| 26 | 3 | 10-F | H | H | H | H | 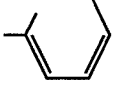 | H |
| 27 | 3 | 10-F | H | H | H | H | 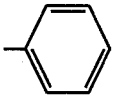 | H |
| 28 | 3 | 10-F | H | H | H | 2-F | 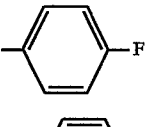 | H |
| 29 | 3 | 10-F | H | H | H | 2-F | 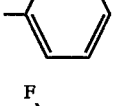 —F | H |
| 30 | 3 | 10-F | H | H | H | 2-OMe | 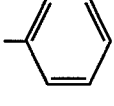 | H |
| 31 | 3 | 10-F | H | H | H | 2-OMe | F 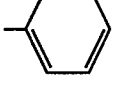 | H |
| 32 | 3 | 10-F | H | H | H | 2-OH | 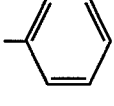 | H |

TABLE 1-continued
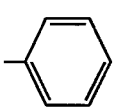
| Compound No. | n | X¹ | X² | X³ | X⁴ | X⁵ | X⁶ | X⁷ |
|---|---|---|---|---|---|---|---|---|
| 33 | 3 | 10-F | H | H | H | 2-Cl | 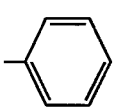 | H |
| 34 | 3 | 10-F | H | H | H | 1-F | 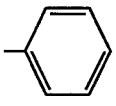 | H |
| 35 | 3 | 10-F | H | H | H | 4-F | 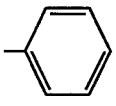 | H |
| 36 | 3 | 10-F | H | H | H | 1-Me | 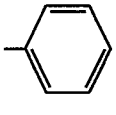 | H |
| 37 | 3 | 10-F | H | H | H | 4-OMe | 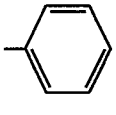 | H |
| 38 | 3 | 10-Br | H | H | H | H | 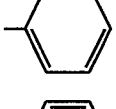 | H |
| 39 | 3 | 11-Cl | H | H | H | H | 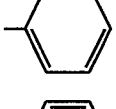 | H |
| 40 | 3 | H | H | H | H | H | 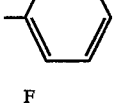 | H |
| 41 | 3 | 9-Cl | H | H | H | H | 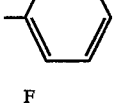 | H |
| 42 | 3 | 9-Cl | 10-F | H | H | H | 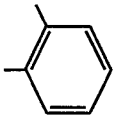 | H |

TABLE 1-continued

[Structure: quinoline with CO₂H, X¹, X², X³, (CH₂)ₙ, and phenyl ring with X⁴, X⁵, X⁶, X⁷ substituents]

| Compound No. | n | X¹ | X² | X³ | X⁴ | X⁵ | X⁶ | X⁷ |
|---|---|---|---|---|---|---|---|---|
| 43 | 3 | 10-F | 11-Cl | H | H | H | (2-fluorophenyl) | H |
| 44 | 3 | 10-F | H | H | H | 2-F | (phenyl) | 4-F |
| 45 | 3 | 10-F | H | H | H | H | (adamantyl) | H |
| 46 | 3 | 10-F | H | H | H | H | (phenyl) | H |

The pharmacological activities of Compound (I) are illustrated with the following test examples.

Test Example 1:
Plaque Forming Cell Assay

The plaque forming cell assay was carried out by the following manner with reference to the method of Jerne et al. [Science, 140, 405 (1963)] and the method of Yamamoto et al. [Drugs Experimental Clinical Research, III(1), 5 (1982)].

Male Balb/c strain mice (7-week-old) (Charles River Co.) were sensitized with 1×10⁸ sheep erythrocytes (product of Biotest Research Institute) administered via the caudal vein, and the spleens were extirpated 6 or 7 days after the sensitization. The extirpated spleens were immersed in Hanks' solution (Nissui Seiyaku) to make a cell suspension, which was then filtered, followed by centrifugal separation at 1200 rpm for 5 minutes. After centrifugal separation, the supernatant was discarded and the precipitate was treated with Tris.NH₄Cl solution to remove the erythrocytes, and then washed three times with Hanks' solution. After discarding the supernatant, the cells were suspended in an RPMI-1640 medium (Nissui Seiyaku) containing 10% bovine fetal serum (Gibco Co.), 50 μg/ml of streptomycin (Meiji Seika), 50 μU/ml of penicillin (Meiji Seika) and 2-mercaptoethanol (5×10⁻⁵M). In each well of a micro culture plate (NUNK Co., Ltd., 24 wells) were put 2 ml the mixture of the cell suspension containing 1×10⁷ of spleen cells, 5×10⁶ sheep erythrocites and a test compound solution (10⁻⁶M) obtained by diluting the test compound dissolved in dimethylsulfoxide (10⁻²M) with the above mentioned RPMI-1640, and the cells were cultured at 37° C. for 5 days.

After the completion of the culturing, the cells were subjected to centrifugal separation at 2000 rpm for 5 minutes, and the resulting supernatant was removed. The precipitate was suspended in 1 ml of Hanks' solution, again subjected to centrifugal separation, suspended in 1 ml of Hanks' solution, and then, 50 μl of the suspension and 50 μl of sheep erythrocytes were added to 400 μl of 0.25% agarose/Hanks' solution heated to 50° C. in advance, and the mixture was scattered on a glass slide, placed on a plaque assay plate, and together with guinea pig complement (Cedarlene Institute) diluted 40-fold with a phosphate buffer solution, incubated at 37° C. for 1 to 2 hours. The number of the appearing direct plaque cells (direct PFC count) in suspension was counted.

The inhibition rate of the antibody production of the test compound was determined by the following equation.

$$\text{inhibition rate (\%)} = \frac{PFC \text{ count in control} - PFC \text{ count in the presence of test compound}}{PFC \text{ count in control}} \times 100$$

The compound used for comparison was 5,6-dihydro-9-fluoro-3-phenylbenz[c]acridine-7-carboxylic acid [Japanese Published Unexamined Patent Application No. 233661/90, hereinafter referred to as Compound (A)] represented by formula (A).

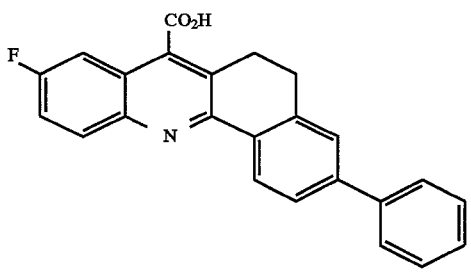

(A)

PFC count in Control means PFC count in the absence of the test compound (dimethylsulfoxide alone).
The results are shown in Table 2.

TABLE 2

| Compound No. | Concentration (M) | Inhibition rate (%) |
|---|---|---|
| 1 | $10^{-5}$ | 98.1 |
|   | $10^{-6}$ | 93.5 |
|   | $10^{-7}$ | 69.2 |
| 2 | $10^{-5}$ | 98.0 |
|   | $10^{-6}$ | 96.3 |
|   | $10^{-7}$ | 86.7 |
| 3 | $10^{-5}$ | 99.7 |
|   | $10^{-6}$ | 99.4 |
|   | $10^{-7}$ | 68.9 |
| 4 | $10^{-5}$ | 99.8 |
|   | $10^{-6}$ | 99.2 |
|   | $10^{-7}$ | 88.4 |
| 13 | $10^{-5}$ | 95.2 |
|   | $10^{-6}$ | 95.7 |
|   | $10^{-7}$ | 82.4 |
| 16 | $10^{-6}$ | 94.1 |
|   | $10^{-7}$ | 88.5 |
|   | $10^{-8}$ | 56.8 |
| 17 | $10^{-6}$ | 91.0 |
|   | $10^{-7}$ | 82.5 |
|   | $10^{-8}$ | 59.8 |
| 28 | $10^{-6}$ | 93.6 |
|   | $10^{-7}$ | 90.1 |
|   | $10^{-8}$ | 73.6 |
| 46 | $10^{-5}$ | 94.9 |
|   | $10^{-6}$ | 84.8 |
|   | $10^{-7}$ | 81.4 |
| A1 | $10^{-5}$ | 78.6 |
|   | $10^{-6}$ | 45.9 |

Test Example 2:
Prophylactic effect against adjuvant arthritis

The experiment was carried out by using groups of 7-weeks-old female Lewis rats (Charles River Co.), each group consisting of 8 rats. Following the method of Newbould B. B. [Brit. J. Pharmacol., 21, 127 (1963)], Mycobacterium butylicum (killed and dried) (Difco Co.) suspended in liquid paraffin (0.6 mg/0.1 ml) was subcutaneously injected, as an adjuvant, into right hind paw of rats, hind paws volumes of which were measured in advance. After the injection, the hind paws volumes were measured using a plethysmograph (Unicom Co., Ltd., TK-101), and the edema ratios were determined by comparing each of the right and left hind paws volumes before the injection with that after the injection.

The test compound was suspended in a 5% arabic gum solution and orally administered once a day on days 0 to 4, days 7 to 11 and days 14 to 16 provided the day of injection of the adjuvant was counted as day 0.

To the control group was orally administered only a 5% arabic gum solution.

After the adjuvant injection, a change in the edema ratio of each group was measured from day 0 to day 18.

The results are shown in FIGS. 1, 2, 3 and 4.

Chronic diseases, which relate to immune response, include rheumarthritis and other autoimmune diseases (systematic erythematodes, psoriatic arthritis, atopic dermatitis and stiff myelitis). In these diseases, various immune abnormalities, such as functional depression of T cells and hyperfunction of B cells, are induced by bacteria, virus or self-antigen. Accordingly, the immunosuppressive agent is a useful medicament against these diseases.

According to the test results, the compound suppressed the T cell-depended antigen production in the PFC reaction and it also has preventive effect on the adjuvant arthritis, which is a typical experimental model for chronic inflammation model. The results suggests that the compound can suppress the T-cell abnormality and the self-antibody production. Thus, the compound is effective on the diseases that cause the immune abnormality.

That is, it was suggested that the compound of this invention exhibits excellent immunosuppressive activity, and is useful as an immunosuppressive agent and as an agent for the treatment of autoimmune disease.

Text Example 3:
Acute toxicity

The test compound was administered to dd mice having a weight of 20 to 25 g per os (p.o.) and intraperitoneally (i.p.). MLD (minimum lethal dose) was evaluated by measuring the mortality after 7 days from the day of administration. The results are shown in Table 3.

TABLE 3

| Compound No. | p.o. | i.p |
|---|---|---|
| 3 | >300 | >100 |
| 4 | >300 | >100 |
| 28 | >100 | >100 |

Depending on the pharmaceutical effects, Compound (I) and its pharmacologically acceptable salt can be used as they are or in various preparation forms for the desired purpose of administration. The pharmaceutical composition of the present invention can be prepared by uniformly mixing an effective amount of Compound (I) or its pharmacologically acceptable salt as an active ingredient with a pharmacologically acceptable carrier. The carrier may be in any of a wide variety of forms, depending on the most preferable form of preparation for administration. The pharmaceutical compositions are preferably in a unit dosage form suitable for oral administration or injection.

In the preparation of pharmaceutical compositions for oral administration, any useful, pharmacologically acceptable carrier can be used. For example, a liquid preparation for oral administration such as suspension and a syrup can be prepared using water; a sugar such as sucrose, sorbitol and fructose; a glycol such as polyethylene glycol and propylene glycol; an oil such as sesame oil, olive oil and soybean oil; an antiseptic such as alkyl p-hydroxybenzoate; and a flavor such as strawberry flavor and peppermint flavor. Powders, pills, capsules and tablets may be prepared using an excipient such as lactose, glucose, sucrose and mannitol; a disintegrator such as starch and sodium alginate; a lubricant such as magnesium stearate and talc; a binder such as polyvinyl alcohol, hydroxypropyl cellulose and gelatin; a surfactant such as fatty acid esters; and a plasticizer such as glycerin. Tablets and capsules are the most useful oral unit dose forms, since their administration is easy. In the preparation of tablets or capsules, a solid pharmacological carrier is used.

A solution for injection may be prepared using a carrier such as distilled water, a saline solution, a glucose solution and a mixture of a saline solution and a glucose solution.

Compound (I) or its pharmaceutically acceptable salts may be administered either orally or parenterally by injection. The effective dose and the administration schedule of Compound (I) or its pharmaceutically acceptable salts vary depending on the mode of administration, age, weight and conditions of a patient, etc. However, it is generally preferred to administer Compound (I) or its pharmaceutically acceptable salts in a dose of 1 to 50 mg/kg per day in 3 to 4 parts.

Explanation of symbols:

—○— is the control group.

—□— is the group to which compound 2 was administered (dose: 10 mg/kg).

—△— is the group to which compound 3 was administered (dose: 10 mg/kg).

Figure 1:
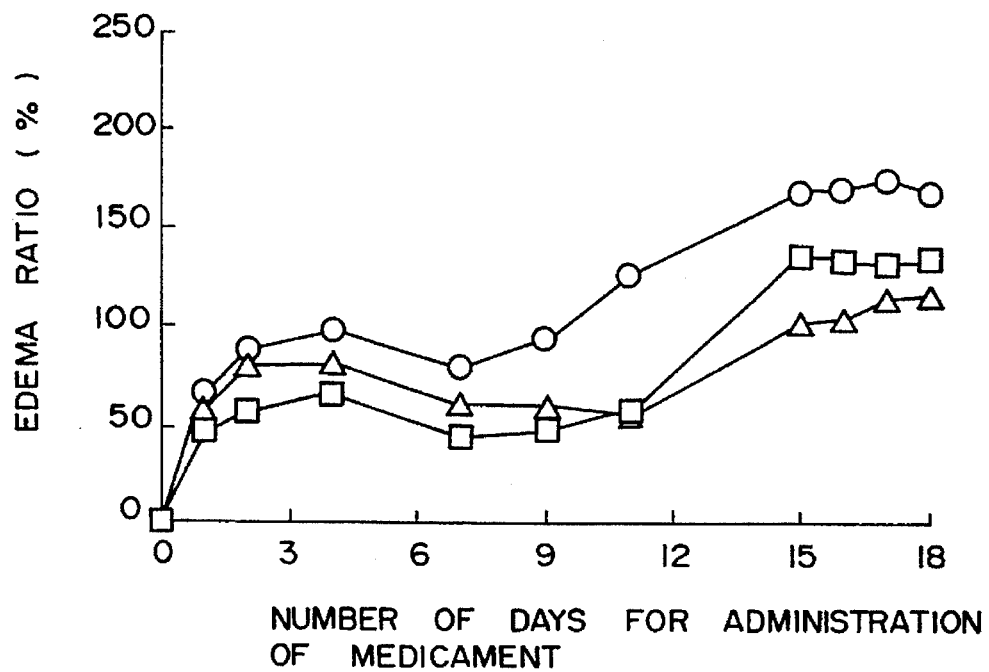
FIG. 1 shows the edema ratios of rats' right hind feet treated with adjuvant.
Figure 2:
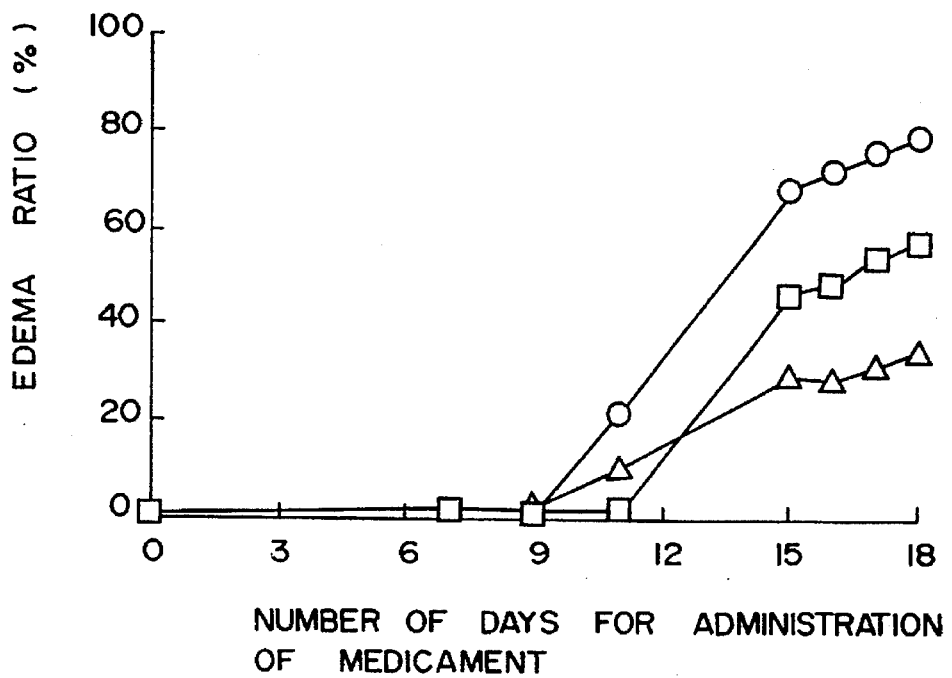

FIG. 2 shows the edema ratios of rats' right hind paw not treated with adjuvant.

Explanation of symbols:

—○— is the control group.

—□— is the group to which compound 2 was administered (dose: 10 mg/kg).

—△— is the group to which compound 3 was administered (dose: 10 mg/kg).

Figure 3:
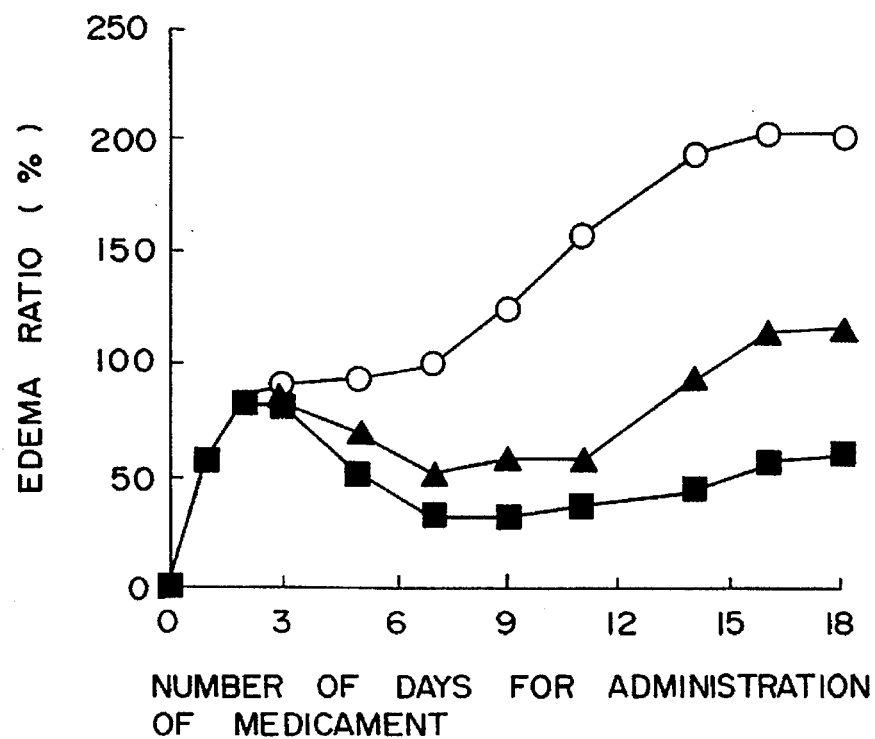

FIG. 3 shows the edema ratios of rats' right hind paw treated with adjuvant.

Explanation of symbols:

—○— is the control group.

—■— is the group to which compound 28 was administered (dose: 0.3 mg/kg).

—▲— is the group to which compound 13 was administered (dose: 0.3 mg/kg).

Figure 4:
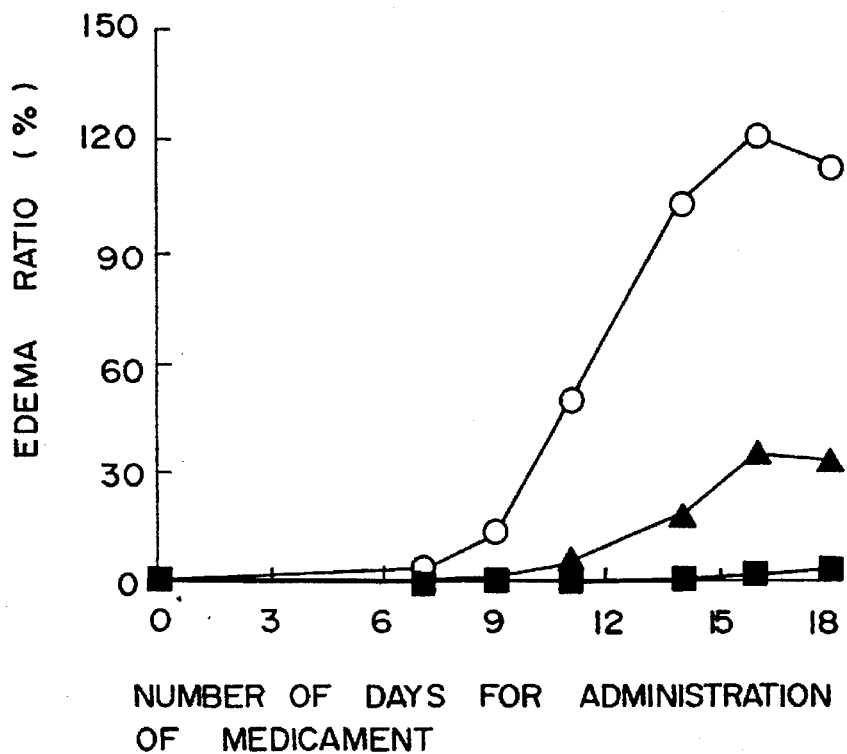

FIG. 4 shows the edema ratios of rats' right hind paw not treated with adjuvant.

Explanation of symbols:

—○— is the control group.

—■— is the group to which compound 28 was administered (dose: 0.3 mg/kg).

—▲— is the group to which compound 13 was administered (dose: 0.3 mg/kg).

This invention will be illustrated more specifically with the use of the following Examples, Preparation Examples and Reference Examples.

EXAMPLE 1:

5,6-Dihydro-9-fluoro-3-(4-fluorophenyl)benz[c]acridine-7-carboxylic acid (Compound 1):

Compound a (1.40 g, 5.8 mmol) obtained in Reference Example 1 and 0.96 g (5.8 mmol) of 5-fluoroisatin were dissolved in 10 ml of ethanol, and 3 ml of water containing 1.63 g (29.1 mmol) of potassium hydroxide was added thereto. After the solution was heat-refluxed for 24 hours, the solvent was distilled off, and the residue was dissolved in water and washed with ether. Hydrochloric acid was added to the aqueous layer, and the precipitated crystals were collected by filtration and washed with ether. The obtained crystals were recrystallized from dimethylformamide-water to obtain 1.54 g of the above-mentioned compound (yield 68%).

Melting point: >300° C. Elemental analysis (%): $C_{24}H_{15}F_2NO_2$ Calculated: C 74.41, H 3.90, N 3.62 Found: C 74.06, H 3.77, N 3.44 IR (KBr)cm$^{-1}$: 1628, 1507, 1369, 1247 NMR (DMSO-d$_6$) δ (ppm): 8.48(1H, d, J=8 Hz), 8.21–8.16(1H, m), 7.84–7.51(6H, m), 7.33(2H, t, J=9 Hz), 3.15–3.07(4H, m) MS (m/e): 387 (M$^+$), 342

EXAMPLE 2:

3-(2,4-Difluorophenyl)-5,6-dihydro-9-fluorobenz [c] acridine-7-carboxylic acid (compound 2):

Compound b (1.91 g, 7.4 mmol) obtained in Reference Example 2 and 1.22 g (7.4 mmol) of 5-fluoroisatin were dissolved in 30 ml of ethanol and a 6N-potassium hydroxide aqueous solution, and the mixture was heat-refluxed for 24 hours. After cooling the reaction mixture, the solvent was distilled off, and the residue was dissolved in water and washed with ether. Hydrochloric acid was added to the aqueous layer, and the precipitated crystals were collected by filtration and washed with ether to obtain 2.1 g of the above-mentioned compound (yield 70%). Said compound was recrystallized from dimethylformamide-water.

Melting point: >291.0°–294.0° C. Elemental analysis (%): $C_{24}H_{14}F_3NO_2$ Calculated: C 71.11, H 3.48, N 3.46 Found: C 71.21, H 3.32, N 3.46 IR (KBr) cm$^{-1}$: 3400, 1710, 1610, 1505, 1434 NMR (DMSO-d$_6$) δ (ppm): 8.51(1H, d, J=8 Hz), 8.22–8.17(1H, m), 7.76–7.21(7H, m), 3.18–3.06 (4H, m) MS (m/e): 405 (M$^+$), 360

EXAMPLE 3:

3-(2,6-Difluorophenyl)-5,6-dihydro-9-fluorobenz[c]acridine-7-carboxylic acid (compound 3):

Compound c (2.20 g, 8.52 mmol) obtained in Reference Example 3 and 1.41 g (8.52 mmol) of 5-fluoroisatin were dissolved in 35 ml of ethanol and 35 ml of a 6N-potassium hydroxide aqueous solution, and the mixture was heat-refluxed for 36 hours. After cooling the reaction mixture, the solvent was distilled off, and the residue was dissolved in water and washed with ether. Hydrochloric acid was added to the aqueous layer, and the precipitated crystals were collected by filtration and washed with ether to obtain 2.79 g (yield 81%) of the above-mentioned compound. Said compound was further recrystallized from dimethylformamide-water.

Melting point: >300° C. Elemental analysis (%): $C_{24}H_{14}F_3NO_2$ Calculated: C 71.11, H 3.48, N 3.46 Found: C 70.87, H 3.47, N 3.57 IR (KBr)cm$^{-1}$: 1710, 1615, 1506, 1468, 1235 NMR (DMSO-d$_6$) δ (ppm): 8.53(1H, d, J=8 Hz), 8.23–8.17(1H, m), 7.77–7.48(5H, m), 7.27(2H, t, J=8 Hz), 3.19–3.06(4H, m) MS (m/e): 405 (M$^+$), 360

EXAMPLE 4:

5,6-Dihydro-9-fluoro-3-(2-thienyl)benz[c]acridine-7-carboxylic acid (compound 4):

Compound d (1.80 g, 7.49 mmol) obtained in Reference Example 4 and 1.24 g (7.49 mmol) of 5-fluoroisatin were dissolved in 30 ml of ethanol and 30 ml of a 6N-potassium hydroxide aqueous solution, and the mixture was heat-refluxed for 20 hours. After cooling the reaction mixture, the solvent was distilled off, and the residue was dissolved in water and washed with ether. Hydrochloric acid was added to the aqueous layer, and the precipitated crystals were collected by filtration and washed with ether. The resulting crystals were recrystallized from dimethylformamide-water to obtain 1.71 g of the above-mentioned compound (yield 61%).

Melting point: >300° C. Elemental analysis (%): $C_{22}H_{14}FNO_2S.0.2H_2O$ Calculated: C 69.72, H 3.83, N 3.70 Found: C 69.69, H 3.76, N 3.89 IR (KBr) $cm^{-1}$: 1605, 1502, 1400, 1360 NMR (DMSO-$d_6$) δ (ppm): 8.45(1H, d, J=8 Hz), 8.19–8.13(1H, m), 7.77–7.48(6H, m), 7.20–7.17(1H, m), 3.18–3.06(4H, m) MS (m/e): 375 ($M^+$), 331

EXAMPLE 5:

5,6-Dihydro-9-fluoro-3-(2-pyridyl)benz[c]acridine-7-carboxylic acid hydrochloride (compound 5):

Compound e (1.38 g, 6.18 mmol) obtained in Reference Example 5 and 1.02 g (6.18 mmol) of 5-fluoroisatin were dissolved in 15 ml of ethanol and 15 ml of a 6N-potassium hydroxide aqueous solution, and the mixture was heat-refluxed for 24 hours. After cooling the reaction mixture, the solvent was distilled off, and the residue was neutralized with dilute hydrochloric acid. The precipitated crystals were collected by filtration. These crystals were then washed with dimethylformamide. Subsequently, the crystals were stirred in a saturated hydrochloric acid methanol solution for 12 hours, and then filtered to obtain 1.86 g of the above-mentioned compound (yield 68%).

Melting point: 300° C. Elemental analysis (%): $C_{23}H_{17}FN_2O_2.2HCl.1.5H_2O$ Calculated: C 58.74, H 4.29, N 5.96 Found: C 58.65, H 4.00, N 5.84 IR (KBr)$cm^{-1}$: 3400, 1708, 1608, 1503, 1247 NMR (DMSO-$d_6$) δ (ppm): 8.86 (1H, d, J=5 Hz), 8.61(1H, d, J=8 Hz), 8.46–8.18(5H, m), 7.86–7.71(2H, m), 7.58–7.54(1H, m), 3.17–3.06(4H, m) MS (m/e): 370 ($M^+$), 325

EXAMPLE 6:

5,6-Dihydro-9-fluoro-3-(3-pyridyl)benz[c]acridine-7-carboxylic acid hydrochloride (compound 6):

Compound f (1.02 g, 4.55 mmol) obtained in Reference Example 6 and 1.02 g (4.55 mmol) of 5-fluoroisatin were dissolved in 15 ml of ethanol and 15 ml of a 6N-potassium hydroxide aqueous solution, and the mixture was heat-refluxed for 24 hours. After cooling the reaction mixture, the solvent was distilled off, and the residue was neutralized with dilute hydrochloric acid. The precipitated crystals were collected by filtration. These crystals were then recrystallized from dimethylformamide-water. Subsequently, the crystals were stirred in a saturated hydrochloric acid methanol solution for 12 hours, and then filtered to obtain 1.29 g of the above-mentioned compound (yield 64%).

Melting point: >300° C. Elemental analysis (%): $C_{23}H_{17}FN_2O_2.2HCl$ Calculated: C 62.32, H 3.87, N 6.32 Found: C 62.16, H 3.76, N 6.24 IR (KBr)$cm^{-1}$: 3400, 2600, 1703, 1614, 1557, 1249 NMR (DMSO-$d_6$) δ (ppm): 9.38 (1H, d, J=2 Hz), 9.01–8.93(2H, m), 8.58(1H, d, J=9 Hz), 8.25–8.15(2H, m), 8.00–7.97(2H, m), 7.78–7.70 (1H, m), 7.57–7.53(1H, m), 3.19–3.13(4H, m) MS (m/e): 370 ($M^+$), 325

EXAMPLE 7:

5,6-Dihydro-9-fluoro-3-(4-pyridyl)benz[c]acridine-7-carboxylic acid hydrochloride (compound 7):

Compound g (1.72 g, 7.71 mmol) obtained in Reference Example 7 and 1.27 g (7.71 mmol) of 5-fluoroisatin were dissolved in 20 ml of ethanol and 20 ml of a 6N-potassium hydroxide aqueous solution, and the mixture was heat-refluxed for 36 hours. After cooling the reaction mixture, the solvent was distilled off, and the residue was neutralized with dilute hydrochloric acid. The precipitated crystals were collected by filtration. These crystals were then washed with dimethylformamide. Subsequently, the crystals were stirred in a saturated hydrochloric acid methanol solution for 12 hours, and then filtered to obtain 2.64 g of the above-mentioned compound (yield 77%).

Melting point: >300° C. Elemental analysis (%): $C_{23}H_{17}FN_2O_2.2HCl.0.5H_2O$ Calculated: C 61.08, H 4.01, N 6.19 Found: C 60.86, H 4.00, N 5.83 IR (KBr)$cm^{-1}$: 3400, 2750, 1710, 1612, 1503, 1346 NMR (DMSO-$d_6$) δ (ppm): 9.02(2H, d, J=7 Hz), 8.62(1H, d, J=9 Hz), 8.52(2H, d, J=7 Hz), 8.26–8.11(3H, m), 7.80–7.72(1H, m), 7.59–7.54 (1H, m), 3.21–3.06(4H, m) MS (m/e): 370 ($M^+$), 325

EXAMPLE 8:

3-Cyclohexyl-5,6-dihydro-9-fluorobenz[c]acridine-7-carboxylic acid (compound 8):

Compound i (1.42 g, 6.22 mmol) obtained in Reference Example 9 and 1.03 g (6.22 mmol) of 5-fluoroisatin were dissolved in 20 ml of ethanol and 20 ml of a 6N-potassium hydroxide aqueous solution, and the mixture was heat-refluxed for 60 hours. After cooling the reaction mixture, the solvent was distilled off, and the residue was dissolved in water and washed with ether. Hydrochloric acid was added to the aqueous layer, and the precipitated crystals were collected by filtration and washed with ether. The resulting crystals were recrystallized from dimethylformamide-water to obtain 1.42 g of the above-mentioned compound (yield 61%).

Melting point: 118.5°–121.0° C. Elemental analysis (%): $C_{24}H_{22}FNO_2.0.2H_2O$ Calculated: C 76.05, H 5.96, N 3.70 Found: C 76.20, H 5.79, N 3.65 IR (KBr)$cm^{-1}$: 2924, 1718, 1610, 1502 NMR (DMSO-$d_6$) δ (ppm): 8.33(1H, d, J=8 Hz), 8.17–8.12(1H, m), 7.73–7.65(1H, m), 7.53–7.48(1H, m), 7.30–7.22(2H, m), 3.12–2.96(4H, m), 2.55(1H, br), 1.81–1.27(10H, m) MS (m/e): 375 ($M^+$), 332

EXAMPLE 9:

5,6-Dihydro-9-ethoxy-3-(2-fluorophenyl)-5-methylbenz[c]acridine-7-carboxylic acid (compound 9):

Compound n (1.07 g, 4.21 mmol) obtained in Reference Example 14 and 0.80 g (4.21 mmol) of 5-ethoxyisatin were dissolved in 15 ml of ethanol and 15 ml of a 6N-potassium hydroxide aqueous solution, and the mixture was heat-refluxed for 24 hours. Thereafter, the solvent was distilled off, and the residue was dissolved in water and washed with ether. Hydrochloric acid was added to the aqueous layer, and the precipitated crystals were collected by filtration and washed with ether. The resulting crystals were recrystallized from dimethylformamide-water to obtain 0.93 g of the above-mentioned compound (yield 52%).

Melting point: 290.0°–300.0° C. Elemental analysis (%): $C_{27}H_{22}FNO_3$ Calculated: C 75.86, H 5.19, N 3.28 Found: C 75.49, H 5.19, N 3.37 IR (KBr) $cm^{-1}$: 1610, 1500, 1375, 1250 NMR (DMSO-$d_6$) δ (ppm): 8.50(1H, d, J=8 Hz), 8.03(1H, d, J=9 Hz), 7.67–7.32(7H, m), 7.10(1H, d, J=3 Hz), 4.16(2H, q, J=7 Hz), 3.26–3.18 (2H, m), 3.02–2.89(1H, m), 1.42(3H, t, J=7 Hz), 1.22(3H, d, J=7 Hz) MS (m/e): 427 ($M^+$), 394

EXAMPLE 10:

5,6-Dihydro-5,5-dimethyl-9-ethoxy-3-(2-fluorophenyl)benz[c]acridine-7-carboxylic acid (compound 10):

Compound q (2.81 g, 10.5 mmol) obtained in Reference Example 17 and 2.00 g (10.5 mmol) of 5-ethoxyisatin were dissolved in 30 ml of ethanol and 30 ml of a 6N-potassium hydroxide aqueous solution, and the mixture was heat-refluxed for 24 hours. The solvent was then distilled off, and the residue was dissolved in water and washed with ether. Hydrochloric acid was added to the aqueous layer, and the precipitated crystals were collected by filtration and washed with ether. The resulting crystals were recrystallized from ethanol to obtain 2.44 g of the above-mentioned compound (yield 53%).

Melting point: >300° C. Elemental analysis (%): $C_{28}H_{24}FNO_3$ Calculated: C 76.17, H 5.48, N 3.17 Found: C 76.16, H 5.58, N 3.34 IR (KBr) $cm^{-1}$: 1621, 1500, 1368, 1252 NMR (DMSO-$d_6$) δ (ppm): 8.54(1H, d, J=8 Hz), 7.99(1H, d, J=9 Hz), 7.67–7.32(7H, m), 7.13(1H, d, J=2 Hz), 4.14(2H, q, J=7 Hz), 2.99(2H, s), 1.41(3H, t, J=7 Hz), 1.31(6H, s) MS (m/e): 441 ($M^+$)

EXAMPLE 11:

6,7-Dihydro-10-fluoro-3-(2-tolyl)-5H-benzo[6,7]cyclohepta[1,2-b]quinoline-8-carboxylic acid (compound 11):

Potassium hydroxide (790 mg, 12.0 mmol) was dissolved in 3 ml of water, and 400 mg (2.40 mmol) of 5-fluoroisatin was added thereto. To this was added 600 mg (2.40 mmol) of compound s obtained in Reference Example 19 which was dissolved in dioxane-ethanol (2 ml–4 ml). The mixture was heat-refluxed for 6 days. The solvent was distilled off, and the residue was dissolved in water and washed with ether. The aqueous layer was filtered through Celite, and acetic acid was added to the flitrate. The precipitated crystals were collected by filtration. These crystals were then dried under reduced pressure, and recrystallized from dimethylformamide-water to obtain 460 mg of the above-mentioned compound (yield 48%).

Melting point: >300° C. Elemental analysis (%): $C_{26}H_{20}FNO_2 \cdot 0.3H_2O$ Calculated: C 77.52, H 5.15, N 3.48 Found: C 77.59, H 4.97, N 3.45 IR (KBr)$cm^{-1}$: 1718, 1628, 1500, 1458 NMR (DMSO-$d_6$) δ (ppm): 8.24–8.18(1H, m), 7.84–7.29(9H, m), 2.67–2.51(4H, m), 2.32(3H, s), 2.25–2.20(2H, m) MS (m/e): 397 ($M^+$)

EXAMPLE 12:

6,7-Dihydro-10-fluoro-3-(2-trifluoromethylphenyl)-5H-benzo[6,7]cyclohepta[1,2-b]quinoline-8-carboxylic acid (compound 12):

Potassium hydroxide (1.30 g, 19.7 mmol) was dissolved in 6 ml of water, and 655 mg (3.95 mmol) of 5-fluoroisatin was added thereto. To this was added 1.20 g (3.95 mmols) of compound t obtained in Reference Example 20 which was dissolved in dioxane-ethanol (3 ml–6 ml). The mixture was heat-refluxed for 6 days. The solvent was distilled off, and the residue was dissolved in water and washed with ether. The aqueous layer was filtered through Celite, and acetic acid was added to the filtrate. The precipitated crystals were collected by filtration. These crystals were then dried under reduced pressure, and recrystallized from dimethylformamide-water to obtain 780 mg of the above-mentioned compound (yield 44%).

Melting point: >300° C. Elemental analysis (%): $C_{26}H_{17}F_4NO_2 \cdot 0.3H_2O$ Calculated: C 68.36, H 3.88, N 3.07 Found: C 68.25, H 3.55, N 2.84 IR (KBr)$cm^{-1}$: 1710, 1625, 1510, 1318, 1170 NMR (DMSO-$d_6$) δ (ppm): 8.25–8.20(1H, m), 7.90–7.33(9H, m), 2.66–2.50(4H, m), 2.24–2.19(2H, m) MS (m/e): 451 ($M^+$)

EXAMPLE 13:

2,10-Difluoro-6,7-dihydro-3-(2-fluorophenyl)-5H-benzo[6,7]cyclohepta[1,2-b]quinoline-8-carboxylic acid (compound 13)

Potassium hydroxide (1.03 g, 15.6 mmol) was dissolved in 6 ml of water, and 520 mg (3.12 mmol) of 5-fluoroisatin was added thereto. To this was added 850 mg (3.12 mmol) of compound x obtained in Reference Example 24 which was dissolved in dioxane-ethanol (3 ml–6 ml). The mixture was heat-refluxed for 6 days. The solvent was distilled off, and the residue was dissolved in water and washed with ether. The aqueous layer was filtered through Celite, and acetic acid was added to the flitrate. The precipitated crystals were collected by filtration. The resulting crystals were dried under reduced pressure, and recrystallized from dimethylformamide-water to obtain 720 mg of the above-mentioned compound (yield 55%).

Melting point: 291.0°–293.5° C. Elemental analysis (%): $C_{25}H_{16}F_3NO_2 \cdot H_2O$ Calculated: C 71.60, H 3.85, N 3.34 Found: C 71.36, H 3.78, N 3.52 IR (KBr)$cm^{-1}$: 1718, 1620, 1500, 1418, 1230 NMR (DMSO-$d_6$) δ (ppm): 8.26–8.20(1H, m), 7.81–7.28(8H, m), 2.89–2.55(4H, m), 2.24–2.19 (2H, m) MS (m/e): 419 ($M^+$)

EXAMPLE 14:

6,7-Dihydro-3-(2-fluorophenyl)-10-methyl-5H-benzo[6,7]cyclohepta[1,2-b]quinoline-8-carboxylic acid (compound 14):

Potassium hydroxide (1.43 g, 21.7 mmol) was dissolved in 6 ml of water, and 670 mg (4.33 mmol) of 5-methylisatin was added thereto. To this was added 1.10 g (4.33 mmol) of compound r obtained in Reference Example 18 which was dissolved in dioxane-ethanol (3 ml-6 ml). The mixture was heat-refluxed for 6 days. The solvent was distilled off, and the residue was dissolved in water and washed with ether. The aqueous layer was filtered through Celite, and acetic acid was added to the filtrate. The precipitated crystals were collected by filtration. These crystals were then dried under reduced pressure, and recrystallized from dimethylformamide-water to obtain 330 mg of the above-mentioned compound (yield 20%).

Melting point: >300° C. Elemental analysis (%): $C_{26}H_{20}FNO_2 \cdot 0.5H_2O$ Calculated: C 76.83, H 5.21, N 3.45 Found: C 76.88, H 4.86, N 3.17 IR (KBr) $cm^{-1}$: 1700, 1624, 1455 NMR (DMSO-$d_6$) δ (ppm): 8.03(1H, d, J=8 Hz), 7.86(1H, d, J=8 Hz), 7.68–7.32(8H, m), 2.89–2.49(7H, m), 2.24–2.18(2H, m) MS (m/e): 397 ($M^+$)

EXAMPLE 15:

11-Fluoro-3-phenyl-5,6,7,8-tetrahydrobenzo[7,8]cycloocta[1,2-b]quinoline-9-carboxylic acid (compound 15):

Using 0.70 g (4.23 mmol) of 5-fluoroisatin and 1.06 g (4.23 mmol) of compound y obtained in Reference Example 25, the same reaction as described in Example 1 was carried out to obtain 0.78 g of the above-mentioned compound (yield 44%).

Elemental analysis (%): $C_{26}H_{20}FNO_2$ Calculated: C 78.57, H 5.07, N 3.52 Found: C 78.40, H 4.98, N 3.53 NMR (DMSO-$d_6$) δ (ppm): 8.20–8.14(1H, m), 7.80–7.38(10H, m), 3.11–2.89(2H, m), 2.32–2.01 (4H, m), 1.81–1.58 (2H, m) MS (m/e): 397 ($M^+$)

EXAMPLE 16:

2,9-Difluoro-5,6-dihydro-3-phenylbenz[c]acridine-7-carboxylic acid (compound 16):

Using 1.21 g (7.33 mmol) of 5-fluoroisatin and 1.76 g (7.33 mmol) of compound z obtained in Reference Example 26, the same reaction as described in Example 1 was carried out to obtain 0.90 g of the above-mentioned compound (yield 32%).

NMR (DMSO-$d_6$) δ (ppm): 8.19(1H, d, J=12 Hz), 8.05–8.00(1H, m), 7.66–7.41(8H, m), 3.10–2.93 (4H, m) MS (m/e): 419 (M$^+$)

EXAMPLE 17:

2,9-Difluoro-5,6-dihydro-3-(2-fluorophenyl)benz[c]acridine-7-carboxylic acid (compound 17):

Using 0.37 g (2.26 mmol) of 5-fluoroisatin and 0.53 g (2.26 mmol) of compound aa obtained in Reference Example 27, the same reaction as described in Example 1 was carried out to obtain 0.54 g of the above-mentioned compound (yield 59%).

Elemental analysis (%): $C_{24}H_{14}F_3NO_2 \cdot 0.5H_2O$ Calculated: C 69.56, H 3.65, N 3.38 Found: C 69.66, H 3.49, N 3.36 NMR (DMSO-$d_6$) δ (ppm): 8.20(1H, d, J=11 Hz), 8.10–8.04(1H, m), 7.69–7.33(7H, m), 3.14–2.94 (4H, m) MS (m/e): 405 (M$^+$)

EXAMPLE 18:

2,9-Difluoro-5,6-dihydro-3-(4-fluorophenyl)benz[c]acridine-7-carboxylic acid (compound 18):

Using 0.57 g (3.45 mmol) of 5-fluoroisatin and 0.89 g (3.45 mmol) of compound bb obtained in Reference Example 28, the same reaction as described in Example 1 was carried out to obtain 0.85 g of the above-mentioned compound (61%).

Elemental analysis (%): $C_{24}H_{14}F_3NO_2 \cdot 0.5H_2O$ Calculated: C 69.56, H 3.65, N 3.38 Found: C 69.45, H 3.38, N 3.45 NMR (DMSO-$d_6$) δ (ppm): 8.23–8.18(2H, m), 7.77–7.33(7H, m), 3.17–3.04(4H, m) MS (m/e): 405 (M$^+$)

EXAMPLE 19:

6,7-Dihydro-10-fluoro-3-(4-fluorophenyl)-5H-benzo[6,7]cyclohepta[1,2-b]quinoline-8-carboxylic acid (compound 19):

Using 863 mg (5.20 mmol) of 5-fluoroisatin and 1.2 g (4.72 mmol) of compound cc obtained in Reference Example 29, the same reaction as described in Example 1 was carried out to obtain 518 mg of the above-mentioned compound (yield 27%).

Melting point: 270° C. (decomp.) Elemental analysis (%): $C_{25}H_{17}F_2NO_2 \cdot 0.3H_2O$ Calculated: C 73.81, H 4.36, N 3.44 Found: C 73.80, H 4.26, N 3.24 NMR (DMSO-$d_6$) δ (ppm): 8.24–8.18(1H, m), 7.86–7.25(9H, m), 2.67–2.59(4H, m), 2.28–2.18 (2H, m) MS (m/e): 389 (M$^+$)

EXAMPLE 20:

6,7-Dihydro-10-fluoro-3-(3-fluorophenyl)-5H-benzo[6,7]cyclohepta[1,2-b]quinoline-8-carboxylic acid (compound 20):

Using 1.13 g (6.76 mmol) of 5-fluoroisatin and 1.56 g (6.14 mmol) of compound dd obtained in Reference Example 30, the same reaction as described in Example 1 was carried out to obtain 658 mg of the above-mentioned compound (yield 27%).

Melting point: >300° C. Elemental analysis (%): $C_{25}H_{17}F_2NO_2$ Calculated: C 74.80, H 4.27, N 3.49 Found: C 74.68, H 4.13, N 3.50 NMR (DMSO-$d_6$) δ (ppm): 8.24–8.19(1H, m), 7.96–7.22(9H, m), 2.65–2.60(4H, m), 2.26–2.22 (2H, m)

EXAMPLE 21:

3-(2,4-Difluorophenyl)-6,7-dihydro-10-fluoro-5H-benzo[6,7]cyclohepta[1,2-b]quinoline-8-carboxylic acid (compound 21):

Using 1.04 mg (6.27 mmol) of 5-fluoroisatin and 1.55 g (5.70 mmol) of compound ee obtained in Reference Example 31, the same reaction as described in Example 1 was carried out to obtain 880 mg of the above-mentioned compound (yield 37%).

Melting point: >300° C. Elemental analysis (%): $C_{25}H_{16}F_3NO_2 \cdot 0.1H_2O$ Calculated: C 71.29, H 3.88, N 3.33 Found: C 71.25, H 3.65, N 3.31 NMR (DMSO-$d_6$) δ (ppm): 8.24–8.19(1H, m), 7.90–7.22(8H, m), 2.70–2.63(4H, m), 2.25–2.20 (2H, m) MS (m/e): 419 (M$^+$)

EXAMPLE 22:

6,7-Dihydro-10-fluoro-3-(4-methoxyphenyl)-5H-benzo[6,7]cyclohepta[1,2-b]quinoline-8-carboxylic acid (compound 22):

Using 1.03 g (6.20 mmol) of 5-fluoroisatin and 1.50 g (5.64 mmol) of compound ff obtained in Reference Example 32, the same reaction as described in Example 1 was carried out to obtain 380 mg of the above-mentioned compound (yield 17%).

Melting point: >300° C. Elemental analysis (%): $C_{26}H_{20}FNO_3 \cdot 0.1H_2O$ Calculated: C 75.20, H 4.90, N 3.37 Found: C 75.06, H 4.87, N 3.31 NMR (DMSO-$d_6$) δ (ppm): 8.23–8.18(1H, m), 7.83–7.54(8H, m), 7.06(1H, d, J=7 Hz), 3.82(3H, s), 2.65–2.58(4H, m), 2.29–2.18(2H, m)

EXAMPLE 23:

6,7-Dihydro-10-fluoro-3-(4-hydroxyphenyl)-5H-benzo[6,7]cyclohepta[1,2-b]quinoline-8-carboxylic acid (compound 23):

Using 883 mg (5.33 mmol) of 5-fluoroisatin and 1.22 g (4.84 mmol) of compound gg obtained in Reference Example 33, the same reaction as described in Example 1 was carried out to obtain 560 mg of the above-mentioned compound (yield 29%).

Elemental analysis (%): $C_{25}H_{18}FNO_3 \cdot 0.4H_2O$ Calculated: C 73.85, H 4.66, N 3.44 Found: C 73.73, H 4.60, N 3.49 NMR (DMSO-$d_6$) δ (ppm): 9.63(1H, s), 8.23–8.17(1H, m), 7.84–7.54(7H, m), 6.89(2H, d, J=8 Hz), 2.75–2.57(4H, m), 2.29–2.17(2H, m)

EXAMPLE 24:

6,7-Dihydro-10-fluoro-3-(2-methoxyphenyl)-5H-benzo[6,7]cyclohepta[1,2-b]quinoline-8-carboxylic acid (compound 24):

Using 760 mg (4.54 mmol) of 5-fluoroisatin and 1.10 g (4.13 mmol) of compound hh obtained in Reference Example 34, the same reaction as described in Example 1 was carried out to obtain 280 mg of the above-mentioned compound (yield 16%).

Melting point: >300° C. Elemental analysis (%): $C_{26}H_{20}FNO_3 \cdot 0.1H_2O$ Calculated: C 75.20, H 4.90, N 3.37 Found: C 75.18, H 5.03, N 3.09 NMR (DMSO-$d_6$) δ (ppm): 8.23–8.17(1H, m), 7.80–7.04(9H, m), 3.32(3H, s), 2.68–2.22(6H, m)

EXAMPLE 25:

6,7-Dihydro-10-fluoro-3-(2-hydroxyphenyl)-5H-benzo[6,7]cyclohepta[1,2-b]quinoline-8-carboxylic acid (compound 25):

Using 652 mg (3.93 mmol) of 5-fluoroisatin and 0.90 g (3.57 mmol) of compound ii obtained in Reference Example 35, the same reaction as described in Example 1 was carried out to obtain 530 mg of the above-mentioned compound (yield 36%).

Melting point: 283°–285° C. Elemental analysis (%): $C_{25}H_{18}FNO_3 \cdot H_2O$ Calculated: C 73.20, H 4.72, N 3.41 Found: C 73.02, H 4.60, N 3.26 NMR (DMSO-$d_6$) δ (ppm): 9.60(1H, s), 7.80–6.89(9H, m), 2.66–2.55(4H, m), 2.32–2.20 (2H, m)

EXAMPLE 26:

6,7-Dihydro-10-fluoro-3-(2-thienyl)-5H-benzo[6,7]cyclohepta[1,2-b]quinoline-8-carboxylic acid (compound 26):

Using 1.09 g (6.59 mmol) of 5-fluoroisatin and 1.45 g (5.99 mmol) of compound jj obtained in Reference Example 36, the same reaction as described in Example 1 was carried out to obtain 733 mg of the above-mentioned compound (yield 31%).

Melting point: >300° C. Elemental analysis (%): $C_{23}H_{16}FNO_2S$ Calculated: C 70.94, H 4.14, N 3.60 Found: C 71.11, H 4.14, N 3.59 NMR (DMSO-$d_6$) δ (ppm): 8.23–8.18(1H, m), 7.82–7.54(7H, m), 7.19(1H, t, J=4 Hz), 2.64–2.57(4H, m), 2.23–2.20(2H, m)

EXAMPLE 27:

6,7-Dihydro-10-fluoro-3-(2-pyridyl)-5H-benzo[6,7]cyclohepta[1,2-b]quinoline-8-carboxylic acid hydrochloride (compound 28):

Using 1.06 g (6.38 mmol) of 5-fluoroisatin and 1.37 g (5.80 mmol) of compound kk obtained in Reference Example 37, the same reaction as described in Example 5 was carried out to obtain 1.82 g of the above-mentioned compound (yield 63%).

Elemental analysis (%): $C_{24}H_{17}FN_2O_2 \cdot 2HCl \cdot 2.4H_2O$ Calculated: C 57.59, H 4.79, N 5.60 Found: C 57.69, H 4.77, N 5.43 NMR (DMSO-$d_6$) δ (ppm): 8.80(1H, d, J=5 Hz), 8.27–8.12(5H, m), 7.94(1H, d, J=8 Hz), 7.81–7.56(3H, m), 2.69–2.64(4H, m), 2.28–2.23 (2H, m)

EXAMPLE 28:

2,10-Difluoro-6,7-dihydro-3-phenyl-5H-benzo[6,7]cyclohepta[1,2-b]quinoline-8-carboxylic acid (compound 28):

Using 720 mg (4.33 mmol) of 5-fluoroisatin and 1.10 g (4.33 mmol) of compound LL obtained in Reference Example 38, the same reaction as described in Example 1 was carried out to obtain 835 mg of the above-mentioned compound (yield 48%).

Melting point: >300° C. Elemental analysis (%): $C_{25}H_{17}F_2NO_2 \cdot 0.2H_2O$ Calculated: C 74.14, H 4.33, N 3.46 Found: C 74.06, H 4.68, N 3.51 IR (KBr) $cm^{-1}$: 1704, 1622, 1502 NMR (DMSO-$d_6$) δ (ppm): 8.26–8.20(1H, m), 7.80–7.42(9H, m), 2.68–2.56(4H, m), 2.37–2.19(2H, m) MS (m/e): 401 (M$^+$)

EXAMPLE 29:

2,10-Difluoro-6,7-dihydro-3-(4-fluorophenyl)-5H-benzo[6,7]cyclohepta[1,2-b]quinoline-8-carboxylic acid (compound 29):

Using 920 mg (5.54 mmol) of 5-fluoroisatin and 1.37 g (5.03 mmol) of compound mm obtained in Reference Example 39, the same reaction as described in Example 1 was carried out to obtain 980 mg of the above-mentioned compound (yield 46%).

Melting point: >300° C. Elemental analysis (%): $C_{25}H_{16}F_3NO_2 \cdot 0.3C_3H_7NO$ Calculated: C 70.45, H 4.14, N 4.13 Found: C 70.46, H 3.84, N 3.99 NMR (DMSO-$d_6$) δ (ppm): 8.25–8.20(1H, m), 7.80–7.33(8H, m), 2.70–2.56(4H, m), 2.24–2.19(2H, m) MS (m/e): 419 (M$^+$)

EXAMPLE 30:

6,7-Dihydro-10-fluoro-2-methoxy-3-phenyl-5H-benzo[6,7]cyclohepta[1,2-b]quinoline-8-carboxylic acid (compound 30):

Using 1.03 (6.20 mmol) of 5-fluoroisatin and 1.50 g (5.64 mmol) of compound oo obtained in Reference Example 41, the same reaction as described in Example 1 was carried out to obtain 1.15 g of the above-mentioned compound (yield 48%).

Melting point: >300° C. Elemental analysis (%): $C_{26}H_{20}FNO_3 \cdot 0.5H_2O$ Calculated: C 73.92, H 5.01, N 3.31 Found: C 73.86, H 4.62, N 3.27 NMR (DMSO-$d_6$) δ (ppm): 8.26–8.21(1H, m), 7.95(1H, s), 7.79–7.29(8H, m), 3.85 (3H, s), 2.66–2.14 (6H, m)

EXAMPLE 31:

6,7-Dihydro-10-fluoro-3-(2-fluorophenyl)-2-methoxy-5H-benzo[6,7]cyclohepta[1,2-b]quinoline-8-carboxylic acid (compound 31):

Using 772 mg (4.65 mmol) of 5-fluoroisatin and 1.20 g (4.23 mmol) of compound pp obtained in Reference Example 42, the same reaction as described in Example 1 was carried out to obtain 265 mg g of the above-mentioned compound (yield 15%).

Elemental analysis (%): $C_{26}H_{19}FNO_3 \cdot 0.3H_2O$ Calculated: C 71.49, H 4.52, N 3.21 Found: C 71.63, H 4.29, N 2.85 NMR (DMSO-$d_6$) δ (ppm): 8.26–8.21(1H, m), 7.79–7.23(8H, m), 3.83(3H, s), 2.69–2.18 (6H, m) MS (m/e): 431 (M$^+$)

EXAMPLE 32:

6,7-Dihydro-10-fluoro-2-hydroxy-3-phenyl-5H-benzo[6,7]cyclohepta[1,2-b]quinoline-8-carboxylic acid (compound 32):

Using 1.25 g (7.55 mmol) of 5-fluoroisatin and 1.73 g (6.86 mmol) of compound qq obtained in Reference Example 43, the same reaction as described in Example 1 was carried out to obtain 427 mg g of the above-mentioned compound (yield 16%).

Melting point: 269.1°–269.2° C. Elemental analysis (%): $C_{25}H_{18}FNO_3 \cdot 0.5H_2O$ Calculated: C 73.52, H 4.69, N 3.43 Found: C 73.61, H 4.27, N 3.27 NMR (DMSO-$d_6$) δ (ppm): 9.66(1H, s), 8.21–8.15(1H, m), 7.77–7.25(9H, m), 2.69–2.13 (6H, m) MS (m/e): 399 (M$^+$)

EXAMPLE 33:

2-Chloro-6,7-dihydro-10-fluoro-3-phenyl-5H-benzo[6,7]cyclohepta[1,2-b]quinoline-8-carboxylic acid (compound 33):

Using 570 mg (3.41 mmol) of 5-fluoroisatin and 0.84 g (3.10 mmol) of compound tt obtained in Reference Example 46, the same reaction as described in Example 1 was carried out to obtain 567 mg g of the above-mentioned compound (yield 44%).

Elemental analysis (%): $C_{25}H_{17}ClFNO_2 \cdot 0.6H_2O$ Calculated: C 70.05, H 4.28, N 3.27 Found: C 69.76, H 4.01, N 3.54 NMR (DMSO-$d_6$) δ (ppm): 8.28–8.20(1H, m), 7.89 (1H, s), 7.81–7.73(1H, m), 7.61–7.39(7H, m), 2.71–2.56 (4H, m), 2.25–2.20(2H, m)

EXAMPLE 34:

1,10-Difluoro-6,7-dihydro-3-phenyl-5H-benzo[6,7]cyclohepta[1,2-b]quinoline-8-carboxylic acid (compound 34):

Using 0.78 g (4.72 mmol) of 5-fluoroisatin and 1.20 g (4.72 mmol) of compound bbb obtained in Reference Example 54, the same reaction as described in Example 1 was carried out to obtain 1.20 g of the above-mentioned compound (63%).

NMR (DMSO-$d_6$) δ (ppm): 8.22–8.17(1H, m), 7.83–7.41 (9H, m), 2.88–2.81(2H, m), 2.52–2.19 (4H, m)

EXAMPLE 35:

4,10-Difluoro-6,7-dihydro-3-phenyl-5H-benzo[6,7]cyclohepta[1,2-b]quinoline-8-carboxylic acid (compound 35):

Using 0.99 g (6.0 mmol) of 5-fluoroisatin and 1.53 g (6.0 mmol) of compound xx obtained in Reference Example 50, the same reaction as described in Example 1 was carried out to obtain 0.78 g of the above-mentioned compound (44%).

Elemental analysis (%): $C_{25}H_{17}F_2NO_2$ Calculated: C 74.80, H 4.27, N 3.49 Found: C 74.64, H 4.18, N 3.42 NMR (DMSO-$d_6$) δ (ppm): 8.25–8.20(1H, m), 7.81–7.42(9H, m), 2.74–2.62(4H, m), 2.25–2.21 (2H, m) MS (m/e): 401 ($M^+$)

EXAMPLE 36:

6,7-Dihydro-10-fluoro-1-methyl-3-phenyl-5H-benzo[6,7]cyclohepta[1,2-b]quinoline-8-carboxylic acid (compound 36):

Using 0.18 g (1.1 mmol) of 5-fluoroisatin and 0.27 g (1.1 mmol) of compound nnn obtained in Reference Example 66, the same reaction as described in Example 1 was carried out to obtain 0.08 g of the above-mentioned compound (19%).

NMR (DMSO-$d_6$) δ (ppm): 8.15–8.05(1H, m), 7.75–7.33 (9H, m), 2.85–2.10(6H, m), 2.42 (3H, s)

EXAMPLE 37:

6,7-Dihydro-10-fluoro-4-methoxy-3-phenyl-5H-benzo[6,7]cyclohepta[1,2-b]quinoline-8-carboxylic acid (compound 37):

Using 0.31 g (1.88 mmol) of 5-fluoroisatin and 0.50 g (1.88 mmol) of compound fff obtained in Reference Example 58, the same reaction as described in Example 1 was carried out to obtain 0.30 g of the above-mentioned compound (39%).

NMR (DMSO-$d_6$) δ (ppm): 8.21–8.15(1H, m), 7.95–7.35 (9H, m), 3.40(3H, s), 2.73–2.62(4H, m), 2.23–2.19(2H, m)

EXAMPLE 38:

10-Bromo-6,7-dihydro-3-(2-fluorophenyl)-5H-benzo[6,7]cyclohepta[1,2-b]quinoline-8-carboxylic acid (compound 38):

Using 980 mg (4.33 mmol) of 5-bromoisatin and 1.0 g (3.93 mmol) of compound r obtained in Reference Example 18, the same reaction as described in Example 1 was carried out to obtain 550 mg of the above-mentioned compound (yield 30%).

Melting point: >300° C. Elemental analysis (%): $C_{25}H_{17}BrFNO_2 \cdot 0.2H_2O$ Calculated: C 64.45, H 3.76, N 3.01 Found: C 64.31, H 3.51, N 3.01 NMR (DMSO-$d_6$) δ (ppm): 8.11–7.86(4H, m), 7.67–7.33(6H, m), 2.69–2.52(4H, m), 2.26–2.01(2H, m)

EXAMPLE 39:

11-Chloro-6,7-dihydro-3-(2-fluorophenyl)-5H-benzo[6,7]cyclohepta[1,2-b]quinoline-8-carboxylic acid (compound 39):

Using 720 mg (3.94 mmol) of 6-chloroisatin and 1.0 g (3.94 mmol) of compound r obtained in Reference Example 18, the same reaction as described in Example 1 was carried out to obtain 383 mg of the above-mentioned compound (yield 23%).

Elemental analysis (%): $C_{25}H_{17}ClFNO_2 \cdot 0.3H_2O$ Calculated: C 70.94, H 4.19, N 3.31 Found: C 71.10, H 4.19, N 3.31 NMR (DMSO-$d_6$) δ (ppm): 8.19–7.33(10H, m), 2.67–2.58(4H, m), 2.25–2.00(2H, m) MS (m/e): 417 (M)

EXAMPLE 40:

6,7-Dihydro-3-2-fluorophenyl)-5H-benzo[6,7]cyclohepta[1,2-b]quinoline-8-carboxylic acid (compound 40):

Using 584 mg (3.94 mmol) of isatin and 1.0 g (3.94 mmol) of compound r obtained in Reference Example 18, the same reaction as described in Example 1 was carried out to obtain 460 mg of the above-mentioned compound (yield 30%).

Elemental analysis (%): $C_{25}H_{18}FN_2O$ Calculated: C 78.31, H 4.73, N 3.65 Found: C 78.31, H 4.65, N 3.68 NMR (DMSO-$d_6$) δ (ppm): 8.15–7.32(11H, m), 2.68–2.59(4H, m), 2.25–2.20(2H, m) MS (m/e): 383 ($M^+$)

EXAMPLE 41:

9-Chloro-6,7-dihydro-3-(2-fluorophenyl)-5H-benzo[6,7]cyclohepta[1,2-b]quinoline-8-carboxylic acid (compound 41):

4-Chloroisatin (1.61 g, 8.87 mmol) and 1.50 g (5.90 mmol) of compound r obtained in Reference Example 18 were dissolved in 30 ml of ethanol, and 0.87 ml (8.87 mmol) of diethylamine was added thereto. The mixture was stirred at room temperature for 24 hours. The precipitate was filtered, washed with ethanol and dried. Then, 20 ml of tetrahydrofuran and 20 ml of conc. hydrochloric acid were added thereto, and the mixture was heat-refluxed for 24 hours. After the solvent was distilled off, water was added to the reaction mixture, and a viscous solid was collected by filtration. The resulting product was washed with methanol to obtain 0.32 g of the above-mentioned compound (yield 13%).

Elemental analysis (%): $C_{25}H_{17}ClFNO_2 \cdot 0.5H_2O$ Calculated: C 70.34, H 4.25, N 3.28 Found: C 70.34, H 4.27, N 3.22 NMR (DMSO-$d_6$) δ (ppm): 8.16–8.12(1H, m), 7.94–7.32(9H, m), 2.66–2.58(4H, m), 2.24–2.19(2H, m)

EXAMPLE 42:

9-Chloro-6,7-dihydro-10-fluoro-3-(2-fluorophenyl)-5H-benzo[6,7]cyclohepta[1,2-b]quinoline-8-carboxylic acid (compound 42):

Using 1.50 g (7.50 mmol) of 4-chloro-5-fluoroisatin and 1.91 g (7.50 mmol) of compound r obtained in Reference Example 18, the same reaction as described in Example 41 was carried out to obtain 0.65 g of the above-mentioned compound (yield 20%).

NMR (DMSO-d$_6$) δ (ppm): 8.24–8.19(1H, m), 7.97–7.89 (2H, m), 7.68–7.33(6H, m), 2.66–2.57(4H, m), 2.24–2.19 (2H, m) MS (m/e): 435 (M$^+$)

EXAMPLE 43:

11-Chloro-6,7-dihydro-10-fluoro-3-(2-fluorophenyl)-5H-benzo[6,7]cyclohepta[1,2-b]quinoline-8-carboxylic acid (compound 43):

Using 1.45 g (7.27 mmol) of 6-chloro-5-fluoroisatin and 1.85 g (7.27 mmol) of compound r obtained in Reference Example 18, the same reaction as described in Example 41 was carried out to obtain 0.41 g of the above-mentioned compound (yield 13%).

NMR (DMSO-d$_6$) δ (ppm): 8.40(1H, d, J=7 Hz), 7.87–7.33(8H, m), 2.67–2.61(4H, m), 2.25–2.19(2H, m) MS (m/e): 435 (M$^+$)

EXAMPLE 44:

6,7-Dihydro-3-phenyl-2,4,10-trifluoro-5H-benzo[6,7]cyclohepta[1,2-b]quinoline-8-carboxylic acid (compound 44):

Using 0.36 g (2.20 mmol) of 5-fluoroisatin and 0.60 g (2.20 mmol) of compound jjj obtained in Reference Example 62, the same reaction as described in Example 1 was carried out to obtain 0.23 g of the above-mentioned compound (yield 40%).

NMR (DMSO-d$_6$) δ (ppm): 8.25–8.19(1H, m), 7.80–7.72 (1H, m), 7.61–7.39(7H, m), 2.71–2.55(4H, m), 2.26–2.18 (2H, m)

EXAMPLE 45:

3-(1-Adamantyl)-6,7-dihydro-10-fluoro-5H-benzo[6,7]cyclohepta[1,2-b]quinoline-8-carboxylic acid (compound 45)

Using 350 mg (2.1 mmol) of 5-fluoroisatin and 560 mg (1.9 mmol) of compound ppp obtained in Reference Example 68, the same reaction as described in Example 1 was carried out to obtain 360 mg of the above-mentioned compound (yield 40%).

NMR (DMSO-d$_6$) δ (ppm): 8.19–8.13(1H, m), 7.76–7.27 (5H, m), 2.95–2.59(4H, m), 2.20–1.60(17H, m)

EXAMPLE 46:

6,7-Dihydro-10-fluoro-3-phenyl-5H-benzo[6,7]cyclohepta[1,2-b]quinoline-8-carboxylic acid (compound 46):

Using 2.16 g (13.0 mmol) of 5-fluoroisatin and 3.07 g (13.0 mmol) of compound kkk obtained in Reference Example 63, the same reaction as described in Example 1 was carried out to obtain 2.0 g of the above-mentioned compound (yield 40%).

Melting point: >300° C. Elemental analysis (%): C$_{25}$H$_{18}$FNO$_2$·0.3H$_2$O Calculated: C 77.23, H 4.82, N 3.60 Found: C 77.14, H 4.52, N 3.63 IR (KBr) cm$^{-1}$: 1715, 1627, 1504 NMR (DMSO-d$_6$) δ (ppm): 8.24–8.19(1H, m), 7.87–7.41(10H, m), 2.66–2.59(4H, m), 2.26–2.22(2H, m) MS (m/e): 383 (M$^+$)

Preparation Example 1: Tablet

A tablet having the following composition was formed by a usual method.

Prescription:

| | |
|---|---|
| Compound 1 | 10 mg |
| Lactose | 30 mg |
| Potato starch | 15 mg |
| Polyvinyl alcohol | 1.5 mg |
| Magnesium stearate | 0.5 mg |

Preparation Example 2: Capsule

A capsule having the following composition was formed by a usual method.

Prescription:

| | |
|---|---|
| Compound 1 | 10 mg |
| Lactose | 100 mg |
| Magnesium stearate | 2.5 mg |

These were mixed and filled into a gelatin capsule.

Preparation Example 3: Injection

An injection having the following composition was formed by a usual method.

Prescription:

| | |
|---|---|
| Compound 1 | 10 mg |
| Sodium chloride | 20 mg |

A distilled water for injection was added to the mixture such that the total amount was 5 ml (for 1 ampule).

Reference Example 1:

3,4-Dihydro-6-(4-fluorophenyl)-1(2H)-naphthalenone (compound a):

1.00 g (3.40 mmol) of 3,4-dihydro-6-trifluoromethylsulfonyloxy-1(2H)-naphthalenone was dissolved in 10 ml of N,N-dimethylformamide in an argon atmosphere, and 1.96 g (5.10 mmol) of 4-fluorophenyltributyltin, 0.43 g (11.0 mmol) of lithium chloride and 0.12 g (0.17 mmol) of bistriphenylphosphine-palladium chloride were added to the solution. The mixture was stirred at 120° C. for 4 hours. The reaction product was cooled to room temperature. Ethyl acetate and a 2M-ammonium fluoride aqueous solution were added thereto, followed by stirring the mixture at room temperature overnight. The precipitate was filtered through Celite, and the filtrate was extracted with ethyl acetate. The organic layer was washed with a saturated sodium chloride aqueous solution, and dried over anhydrous magnesium sulfate. After the solvent was distilled off under reduced pressure, the residue was purified by silica-gel column chromatography (eluent: a mixture of 3% ethyl acetate and hexane) to obtain 0.65 g of the above-mentioned compound (yield 80%).

NMR (CDCl$_3$) δ (ppm): 8.09(1H, d, J=8 Hz), 7.61–7.42 (4H, m), 7.14(2H, t, J=9 Hz), 3.02(2H, t, J=6 Hz), 2.69(2H, t, J=6 Hz), 2.22–2.13 (2H, m) MS (m/e): 240 (M$^+$), 212

Reference Example 2:

6-(2,4-Difluorophenyl)-3,4-dihydro-1(2H)-naphthalenone (compound b):

1.00 g (3.40 mmol) of 3,4-dihydro-6-trifluoromethylsulfonyloxy-1(2H)-naphthalenone was dissolved in 10 ml of N,N-dimethylformamide in an argon atmosphere, and 2.05 g (5.10 mmol) of 2,4-difluorophenyltributyltin, 0.43 g (11.0 mmol) of lithium chloride, 0.12 g (0.17 mmol) of bistriphenylphosphinepalladium chloride and 0.04 g (0.17 mmol) of silver oxide were added to the solution. The mixture was stirred at 120° C. for 1 hour. The reaction product was cooled to room temperature. Ethyl acetate and a 2M-ammonium fluoride aqueous solution were added thereto, followed by stirring the mixture at room temperature overnight. The precipitate was filtered through Celite, and the filtrate was extracted with ethyl acetate. The organic layer was washed with a saturated sodium chloride aqueous solution, and dried over anhydrous magnesium sulfate. After the solvent was distilled off under reduced pressure, the residue was purified by silica-gel column chromatography (eluent: a mixture of 3% ethyl acetate and hexane) to obtain 0.47 g of the above-mentioned compound (yield 54%).

NMR (CDCl$_3$) δ (ppm): 8.10(1H, d, J=8 Hz), 7.46–7.38 (3H, m), 7.01–6.88(2H, m), 3.02(2H, t, J=6 Hz), 2.69(2H, t, J=6 Hz), 2.22–2.13 (2H, m) MS (m/e): 258 (M$^+$), 230

Reference Example 3:

6-(2,6-Difluorophenyl)-3,4-dihydro-1(2H)-naphthalenone (compound c):

1.00 g (3.40 mmol) of 3,4-dihydro-6-trifluoromethylsulfonyloxy-1(2H)-naphthalenone was dissolved in 10 ml of N,N-dimethylformamide in an argon atmosphere, and 2.05 g (5.10 mmol) of 2,6-difluorophenyltributyltin, 0.43 g (11.0 mmol) of lithium chloride, 0.12 g (0.17 mmol) of bistriphenylphosphinepalladium chloride and 0.04 g (0.17 mmol) of silver oxide were added to the solution. The mixture was stirred at 120° C. for 1 hour. The reaction product was cooled to room temperature. Ethyl acetate and a 2M-ammonium fluoride aqueous solution were added thereto, followed by stirring the mixture at room temperature overnight. The precipitate was filtered through Celite, and the filtrate was extracted with ethyl acetate. The organic layer was washed with a saturated sodium chloride aqueous solution, and dried over anhydrous magnesium sulfate. After the solvent was distilled off under reduced pressure, the residue was purified by silica-gel column chromatography (eluent: a mixture of 3% ethyl acetate and hexane) to obtain 0.75 g of the above-mentioned compound (yield 85%).

NMR (CDCl$_3$) δ (ppm): 8.12(1H, d, J=8 Hz), 7.43–7.27 (3H, m), 7.00(2H, t, J=8 Hz), 3.03(2H, t, J=6 Hz), 2.70(2H, t, J=6 Hz), 2.24–2.14 (2H, m) MS (m/e): 258 (M$^+$), 230

Reference Example 4:

3,4-Dihydro-6-(2-thienyl)-1(2H)-naphthalenone (compound d):

3,4-Dihydro-6-trifluoromethylsulfonyloxy-1(2H)-naphthalenone (3.96 g, 13.5 mmol) was dissolved in 40 ml of N,N-dimethylformamide in an argon atmosphere, and 6.03 g (16.1 mmol) of 2-thienyltributyltin, 1.71 g (40.4 mmol) of lithium chloride and 0.47 g (0.67 mmol) of bistriphenylphosphinepalladium chloride were added to the solution. The mixture was stirred at 120° C. for 4 hours. The reaction product was cooled to room temperature. Ethyl acetate and a 2M-ammonium fluoride aqueous solution were added thereto, followed by stirring the mixture at room temperature overnight. The precipitate was filtered through Celite, and the filtrate was extracted with ethyl acetate. The organic layer was washed with a saturated sodium chloride aqueous solution, and dried over anhydrous magnesium sulfate. After the solvent was distilled off under reduced pressure, the residue was purified by silica-gel column chromatography (eluent: a mixture of 20% ethyl acetate and hexane) to obtain 2.44 g of the above-mentioned compound (yield 79%). NMR (CDCl$_3$) δ (ppm): 8.04(1H, d, J=8 Hz), 7.57–7.35(4H, m), 7.13–7.11(1H, m), 2.99(2H, t, J=6 Hz), 2.67(2H, t, J=6 Hz), 2.21–2.11 (2H, m) MS (m/e): 228 (M$^+$), 200

Reference Example 5:

3,4-Dihydro-6-(2-pyridyl)-1(2H)-naphthalenone (compound e):

3,4-Dihydro-6-trifluoromethylsulfonyloxy-1(2H)-naphthalenone (2.40 g, 8.17 mmol) was dissolved in 25 ml of N,N-dimethylformamide in an argon atmosphere, and 3.65 g (9.91 mmol) of 2-pyridyltributyltin, 1.04 g (24.5 mmol) of lithium chloride and 0.29 g (0.41 mmol) of bistriphenylphosphinepalladium chloride were added to the solution. The mixture was stirred at 120° C. for 4 hours. The reaction product was cooled to room temperature. Ethyl acetate and a 2M-ammonium fluoride aqueous solution were added thereto, followed by stirring the mixture at room temperature overnight. The precipitate was filtered through Celite, and the filtrate was extracted with ethyl acetate. The organic layer was washed with a saturated sodium chloride aqueous solution, and dried over anhydrous magnesium sulfate. After the solvent was distilled off under reduced pressure, the residue was purified by silica-gel column chromatography (eluent: a mixture of 30% ethyl acetate and hexane) to obtain 0.93 g of the above-mentioned compound (yield 51%).

NMR (CDCl$_3$) δ (ppm): 8.74–8.71(1H, m), 8.14(1H, d, J=8 Hz), 7.95–7.76(4H, m), 7.31–7.28(1H, m), 3.06(2H, t, J=6 Hz), 2.70(2H, t, J=6 Hz), 2.22–2.13(2H, m) MS (m/e): 223 (M$^+$), 195

Reference Example 6:

3,4-Dihydro-6-(3-pyridyl)-1(2H)-naphthalenone (compound f):

3,4-Dihydro-6-trifluoromethylsulfonyloxy-1(2H)-naphthalenone (1.15 g, 3.91 mmol) was dissolved in 12 ml of N,N-dimethylformamide in an argon atmosphere, and 1.75 g (4.75 mmol) of 3-pyridyltributyltin, 0.50 g (11.7 mmol) of lithium chloride and 0.14 g (0.20 mmol) of bistriphenylphosphinepalladium chloride were added to the solution. The mixture was stirred at 120° C. for 4 hours. The reaction product was cooled to room temperature, and ethyl acetate and a 2M-ammonium fluoride aqueous solution were added thereto, followed by stirring the mixture at room temperature overnight. The precipitate was filtered through Celite, and the filtrate was extracted with ethyl acetate. The organic layer was washed with a saturated sodium chloride aqueous solution, and dried over anhydrous magnesium sulfate. After the solvent was distilled off under reduced pressure, the residue was purified by silica-gel column chromatography (eluent: a mixture of 30% ethyl acetate and hexane) to obtain 0.80 g of the above-mentioned compound (yield 92%).

NMR (CDCl$_3$) δ (ppm): 8.88(1H, t, J=1 Hz), 8.65–8.63 (1H, m), 8.14(1H, d, J=8 Hz), 7.93–7.88(1H, m), 7.54–7.37 (3H, m), 3.05(2H, t, J=6 Hz), 2.70(2H, t, J=6 Hz), 2.24–2.15 (2H, m) MS (m/e): 223 (M$^+$), 195

Reference Example 7:

3,4-Dihydro-6-(4-pyridyl)-1(2H)-naphthalenone (compound g):

3,4-Dihydro-6-trifluoromethylsulfonyloxy-1(2H)-naphthalenone (4.41 g, 15.0 mmol) was dissolved in 40 ml of N,N-dimethylformamide in an argon atmosphere, and 6.77 g (18.4 mmol) of 4-pyridyltributyltin, 1.90 g (45.0 mmol) of lithium chloride and 0.53 g (0.75 mmol) of bistriphenylphosphinepalladium chloride were added to the solution. The mixture was stirred at 120° C. for 4 hours. The reaction product was cooled to room temperature, and ethyl acetate and a 2M-ammonium fluoride aqueous solution were added thereto, followed by stirring the mixture at room temperature overnight. The precipitate was filtered through Celite, and the filtrate was extracted with ethyl acetate. The organic layer was washed with a saturated sodium chloride aqueous solution, and dried over anhydrous magnesium sulfate. After the solvent was distilled off under reduced pressure, the residue was purified by silica-gel column chromatography (eluent: a mixture of 30% ethyl acetate and hexane) to obtain 2.32 g of the above-mentioned compound (yield 69%).

NMR (CDCl$_3$) δ (ppm): 8.72–8.68(2H, m), 8.14(1H, d, J=8 Hz), 7.60–7.50(4H, m), 3.05(2H, t, J=6 Hz), 2.71(2H, t, J=6 Hz), 2.26–2.14 (2H, m) MS (m/e): 223 (M$^+$), 195

Reference Example 8:

3,4-Dihydro-6-(1-cyclohexenyl)-1(2H)-naphthalenone (compound h):

3,4-Dihydro-6-trifluoromethylsulfonyloxy-1(2H)-naphthalenone (5.30 g, 18.0 mmol) was dissolved in 50 ml of N,N-dimethylformamide in an argon atmosphere, and 8.69 g (23.4 mmol) of 1-cyclohexenyltributyltin, 2.28 g (54.0 mmol) of lithium chloride and 0.63 g (0.90 mmol) of bistriphenylphosphinepalladium chloride were added to the solution. The mixture was stirred at 120° C. for 4 hours. The reaction product was cooled to room temperature, and ethyl acetate and a 2M-ammonium fluoride aqueous solution were added thereto, followed by stirring the mixture at room temperature overnight. The precipitate was filtered through Celite, and the filtrate was extracted with ethyl acetate. The organic layer was washed with a saturated sodium chloride aqueous solution, and dried over anhydrous magnesium sulfate. After the solvent was distilled off under reduced pressure, the residue was purified by silica-gel column chromatography (eluent: a mixture of 2% ethyl acetate and hexane) to obtain 2.32 g of the above-mentioned compound (yield 57%).

NMR (CDCl$_3$) δ (ppm): 7.96(1H, d, J=8 Hz), 7.33–7.23 (2H, m), 6.27–6.24(1H, m), 2.95(2H, t, J=6 Hz), 2.63(2H, t, J=6 Hz), 2.43–1.62 (10H, m) MS (m/e): 226 (M$^+$), 198

Reference Example 9:

3,4-Dihydro-6-(1-cyclohexenyl)-1(2H)-naphthalenone (compound i):

Compound h (1.50 g, 6.63 mmol) obtained in Reference Example 8 was dissolved in 30 ml of ethanol, and 75 mg of palladium/carbon was added thereto, followed by stirring the mixture in a hydrogen atmosphere at room temperature for 4 hours. The reaction mixture was filtered through Celite, and the solvent was distilled off to obtain 1.42 g (94 %) of the above-mentioned compound.

NMR (CDCl$_3$) δ (ppm): 7.96(1H, d, J=8 Hz), 7.16–7.07 (2H, m), 2.93(2H, t, J=6 Hz), 2.62(2H, t, J=6 Hz), 2.52(1H, br), 2.17–1.27 (12H, m) MS (m/e): 228 (M$^+$), 200

Reference Example 10:

3-[4-(2-Fluorophenyl)benzoyl]propanoic acid (compound j):

Aluminum trichloride (6.2 g, 46.5 mmol) was suspended in 50 ml of dichloroethane, and 3.02 g (30.2 mmol) of succinic anhydride and 4.0 g (23.2 mmol) of 2-fluorobiphenyl were added thereto, followed by stirring the mixture at room temperature for 4 hours. The reaction solution was poured in hydrochloric acid containing ice, and extracted with chloroform. The organic layer was washed with water, and dried over anhydrous magnesium sulfate. After the solvent was distilled off under reduced pressure, the residue was recrystallized from chloroform to obtain 5.6 g of the above-mentioned compound (yield 89%).

NMR (CDCl$_3$) δ (ppm): 8.15(2H, d, J=7 Hz), 7.73–7.00 (7H, m), 3.35(2H, t, J=7 Hz), 2.85 (2H, t, J=7 Hz) MS (m/e): 272 (M$^+$), 255, 228

Reference Example 11:

4-[4-(2-Fluorophenyl)phenyl]butanoic acid (compound k):

Compound j (5.21 g, 19.1 mmol) obtained in Reference Example 10 was dissolved in 25 ml of trifluoroacetic acid, and 7.5 ml (46.5 mmol) of triethylsilane was added thereto, followed by stirring the mixture at 70° C. for 6 hours. After the solvent was distilled off, the residue was poured into water, and extracted with chloroform. The organic layer was washed with water, and dried over anhydrous magnesium sulfate. After the solvent was distilled off under reduced pressure, the residue was separated and purified by silica-gel column chromatography [eluent: a mixture of ethyl acetate and hexane (4:1)] to obtain 4.72 g of the above-mentioned compound (yield 97%).

NMR (CDCl$_3$) δ (ppm): 7.65–6.93(8H, m), 2.80(2H, t, J=6 Hz), 2.31(2H, t, J=6 Hz), 2.21–1.81(2H, m) MS (m/e): 258 (M$^+$)

Reference Example 12:

3,4-Dihydro-7-(2-fluorophenyl)-1(2H)-naphthalenone (compound L):

50 ml of polyphosphoric acid was added to 4.72 g (18.4 mmol) of compound k obtained in Reference Example 11, and the mixture was stirred at 70° C. for 4 hours. The reaction product was poured into ice water, and extracted with chloroform. The organic layer was washed with water, and dried over anhydrous magnesium sulfate. The solvent was distilled off under reduced pressure to obtain 4.11 g of the above-mentioned compound (yield 94%).

NMR (CDCl$_3$) δ (ppm): 8.15(1H, s), 7.71–6.90(6H, m), 2.93(2H, t, J=5 Hz), 2.60(2H, t, J=5 Hz), 2.30–1.92(2H, m) MS (m/e): 240 (M$^+$)

Reference Example 13:

7-(2-Fluorophenyl)-1-methyl-1,2,3,4-tetrahydronaphthalene (compound m):

To Dimethyl sulfoxide (12 ml) was added 1.0 g (25.0 mmol) of 60% sodium hydride, and the mixture was stirred at 60° C. for 1 hour. After the mixture was cooled to room temperature, 9.08 g (25.4 mmol) of methyltriphenylphosphonium bromide and 12 ml of tetrahydrofuran were added thereto, followed by stirring the resulting mixture at room temperature for 20 minutes. Further, 3.00 g (12.5 mmol) of compound L obtained in Reference Example 12, which was dissolved in 15 ml of tetrahydrofuran, was added thereto, and the mixture was stirred at room temperature for 3 hours. A reaction solution was poured into water, and extracted with ether. The organic layer was washed with a sodium chloride aqueous solution, and dried over anhydrous magnesium sulfate. The solvent was distilled off under reduced pressure. The residue was dissolved in 30 ml of ethanol, and 150 mg of palladium/carbon was added thereto, followed by stirring the mixture in a hydrogen atmosphere at room temperature for 4 hours. The reaction mixture was filtered through Celite. After the solvent was distilled off, the residue was separated and purified by silica-gel column chromatography [eluent: hexane] to obtain 1.80 g (60%) of the above-mentioned compound.

NMR (CDCl$_3$) δ (ppm): 7.45–7.09(7H, m), 3.00–2.78 (3H, m), 1.98–1.53(4H, m), 1.33(3H, d, J=7 Hz) MS (m/e): 240 (M$^+$), 225

Reference Example 14:

3,4-Dihydro-6-(2-fluorophenyl)-4-methyl-1(2H)-naphthalenone (compound n):

Compound m (1.85 g, 7.7 mmol) obtained in Reference Example 13 was dissolved in 3 ml of propionic acid and 10 ml of acetic acid, and 2.5 g (25 mmol) of chromic acid dissolved in 12 ml of a mixture of acetic acid and water (7:1) was added thereto at 0° C., followed by stirring the mixture at room temperature for 4 hours. The reaction solution was poured into a sodium sulfite aqueous solution, and extracted with ethyl acetate. The organic layer was washed with a sodium chloride aqueous solution, and dried over anhydrous magnesium sulfate. After the solvent was distilled off under reduced pressure, the residue was separated and purified by silica-gel column chromatography [eluent: a mixture of hexane and ethyl acetate (in a ratio 10:1)] to obtain 0.88 g of the above-mentioned compound (yield 45%).

NMR (CDCl$_3$) δ (ppm): 8.10(1H, d, J=8 Hz), 7.51–7.13 (6H, m), 3.19–1.88(5H, m), 1.43(3H, d, J=7 Hz) MS (m/e): 254 (M$^+$), 226

Reference Example 15:

5-[4-(2-Fluorophenyl)phenyl]-2-methyl-2-pentanol (compound o):

Compound k (5.00 g, 19.4 mmol) obtained in Reference Example 11 was dissolved in 50 ml of tetrahydrofuran, and 40 ml (120 mmol) of an ether solution containing 3 mol of methylmagnesium bromide were added at 0° C., followed by heat-refluxing the mixture for 1 hour. The reaction solution was poured into an ammonium chloride aqueous solution, and extracted with ether. The organic layer was washed with a sodium chloride aqueous solution, and dried over anhydrous magnesium sulfate. After the solvent was distilled off under reduced pressure, the residue was separated and purified by silica-gel column chromatography [eluent: a mixture of ethyl acetate and hexane (8:1)] to obtain 3.67 g of the above-mentioned compound (yield 70%).

NMR (CDCl$_3$) δ (ppm): 7.49–7.09(7H, m), 2.66(2H, t, J=7 Hz), 1.78–1.51(m, 4H), 1.21 (s, 6H) MS (m/e): 258 (M$^+$), 199

Reference Example 16:

7-(2-Fluorophenyl)-1,1-dimethyl-1,2,3,4-tetrahydronaphthalene (compound p):

Compound o (3.67 g, 13.5 mmol) obtained in Reference Example 15 was dissolved in 40 ml of dichloroethane, and 2.0 g (15.0 mmol) of aluminum trichloride was added thereto, followed by stirring the mixture at room temperature for 30 minutes. The reaction product was poured into ice water, and extracted with chloroform. The organic layer was washed with a sodium chloride aqueous solution, and dried over anhydrous magnesium sulfate. After the solvent was distilled off under reduced pressure, the residue was extracted with chloroform and with water. The organic layer was washed with water, and dried over anhydrous magnesium sulfate. After the solvent was distilled off, the residue was separated and purified by silica-gel column chromatography [eluent: hexane] to obtain 3.00 g of the above-mentioned compound (yield 88%).

NMR (CDCl$_3$) δ (ppm): 7.77–7.33(7H, m), 3.05(2H, t, J=6 Hz), 2.10–1.92(4H, m), 1.58(6H, s) MS (m/e): 254 (M$^+$), 239

Reference Example 17:

3,4-Dihydro-4,4-dimethyl-6-(2-fluorophenyl)-1(2H)-naphthalenone (compound q):

Compound p (2.80 g, 11.1 mmol) obtained in Reference Example 16 was dissolved in 3.5 ml of propionic acid and 17 ml of acetic acid, 3.54 g (35.4 mmol) of chromic acid dissolved in 14 ml of a mixture of acetic acid and water (7:1) was added thereto at 0° C., followed by stirring the mixture at room temperature for 4 hours. The reaction solution was poured into a sodium sulfite aqueous solution, and extracted with ethyl acetate. The organic layer was washed with a sodium chloride aqueous solution, and dried over anhydrous magnesium sulfate. After the solvent was distilled off under reduced pressure, the residue was separated and purified by silica-gel column chromatography [eluent: a mixture of hexane and ethyl acetate (10:1)] to obtain 2.25 g of the above-mentioned compound (yield 76%).

NMR (CDCl$_3$) δ (ppm): 8.09(1H, d, J=8 Hz), 7.61–7.14 (6H, m), 2.76(t, J=6 Hz), 2.06(2H, t, J=6 Hz), 1.44( 6H, s) MS (m/e): 268 (M$^+$), 253, 225

Reference Example 18:

7-(2-Fluorophenyl)-1-benzsuberone (compound r):

14.0 g (55.6 mmol) of 7-bromo-1-benzsuberone was dissolved in 50 ml of dimethylformamide in an argon atmosphere, and 3.2 g (2.78 mmol) of tetrakistriphenylphosphinepalladium and 12.8 g (55.6 mmols) of silver oxide were added thereto, followed by stirring the mixture at 100° C. for 10 minutes. To the reaction solution was added 25.9 g (66.7 mmol) of (2-fluorophenyl)tributyltin dissolved in 15 ml of dimethylformamide, and the mixture was stirred at 120° C. for 2 hours. The reaction solution was cooled to room temperature, and ethyl acetate and a 2M-ammonium fluoride aqueous solution were added thereto. The mixture was stirred at room temperature for 1 hour. The precipitate was filtered through Celite, and the filtrate was extracted with ethyl acetate. The organic layer was washed with a saturated sodium chloride aqueous solution, and dried over anhydrous magnesium sulfate. The resulting product was purified by silica-gel column chromatography (eluent: a mixture of 3% ethyl acetate and hexane) to obtain 9.02 g of the above-mentioned compound (yield 64%).

NMR (CDCl$_3$) δ (ppm): 7.82(1H, d, J=8 Hz), 7.51–7.12 (6H, m), 2.99(t, J=6 Hz, 2H), 2.77 (2H, t, J=6 Hz), 1.95–1.81 (4H, m) MS (m/e): 254 (M$^+$)

Reference Example 19:

7-(2-Tolyl)-1-benzsuberone (compound s):

7-Bromo-1-benzsuberone (1.80 g, 7.14 mmol) was dissolved in 10 ml of dimethylformamide in an argon atmosphere, and 247 mg (0.21 mmol) of tetrakistriphenylphosphinepalladium and 1.65 g (7.14 mmol) of silver oxide were added thereto, followed by stirring the mixture at 100° C. for 10 minutes. To the reaction solution was added 4.08 g (10.7 mmol) of (2-tolyl)tributyltin dissolved in 10 ml of dimethylformamide, and the mixture was stirred at 120° C. for 4 hours. The reaction solution was cooled to room temperature, and ethyl acetate and a 2M-ammonium fluoride aqueous solution were added thereto. The mixture was stirred at room temperature for 1 hour. The precipitate was filtered through Celite, and the filtrate was extracted with ethyl acetate. The organic layer was washed with a saturated sodium chloride aqueous solution, and dried over anhydrous magnesium sulfate. The resulting product was purified by silica-gel column chromatography (eluent: a mixture of 3% ethyl acetate and hexane) to obtain 970 mg of the above-mentioned compound (yield 55%).

NMR (CDCl$_3$) δ (ppm): 7.79(1H, d, J=8 Hz), 7.27–7.20 (5H, m), 7.15(1H, s), 2.97(2H, t, J=6 Hz), 2.77(2H, t, J=6 Hz), 1.94–1.83(4H, m) MS (m/e): 250 (M$^+$)

Reference Example 20:

7-(2-Trifluoromethylphenyl)-1-benzsuberone (compound t):

2.00 g (7.93 mmol) of 7-bromo-1-benzsuberone was dissolved in 10 ml of dimethylformamide in an argon atmosphere, and 274 mg (0.24 mmol) of tetrakistriphenylphosphinepalladium and 1.84 g (7.93 mmol) of silver oxide were added thereto, followed by stirring the mixture at 100° C. for 10 minutes. To the reaction solution was added 5.19 g (11.9 mmol) of (2-trifluorophenyl)tributyltin dissolved in 10 ml of dimethylformamide, and the mixture was stirred at 120° C. for 3 hours. The reaction solution was cooled to room temperature, and ethyl acetate and a 2M-ammonium fluoride aqueous solution were added thereto. The mixture was stirred at room temperature for 1 hour. The precipitate was filtered through Celite, and the filtrate was extracted with ethyl acetate. The organic layer was washed with a saturated sodium chloride aqueous solution, and dried over anhydrous magnesium sulfate. The resulting product was purified by silica-gel column chromatography (eluent: a mixture of 3% ethyl acetate and hexane) to obtain 1.72 mg of the above-mentioned compound (yield 72%).

NMR (CDCl$_3$) δ (ppm): 7.79–7.74(2H, m), 7.60–7.46 (2H, m), 7.34–7.25(2H, m), 7.18(1H, s), 2.97(2H, t, J=6 Hz), 2.78(2H, t, J=6 Hz), 1.96–1.82(4H, m) MS (m/e): 304 (M$^+$)

Reference Example 21:

Methyl 4-(3-bromo-4-fluorobenzoyl)butyrate (compound u):

To 15 g (85.7 mmol) of 2-bromofluorobenzene were added 100 ml of 1,2-dichloroethane and 22.9 g (171.4 mmol) of ammonium trichloride. Methyl 4- (chloroformyl) butyrate (13 ml, 94.3 mmol) was added thereto while stirring. After the mixture was heat-refluxed for 10 hours, the reaction mixture was poured into hydrochloric acid containing ice, and extracted with chloroform. The organic layer was washed with hydrochloric acid, dried over anhydrous sodium sulfate, and recrystallized from hexane to obtain 13.6 g of the above-mentioned compound (yield 53%).

NMR (CDCl$_3$) δ (ppm): 8.19(1H, d, J=7 Hz), 7.95–7.89 (1H, m), 7.20(1H, t, J=8 Hz), 3.69(3H, s), 3.02(2H, t, J=7 Hz), 2.45(2H, t, J=7 Hz), 2.12–2.01 (2H, m) MS (m/e): 302, 304 (M$^+$)

Reference Example 22:

Methyl 4-[(4-fluoro-3-(2-fluorophenyl)benzoyl)] butyrate (compound v):

Compound u (3.00 g, 10.0 mmol) obtained in Reference Example 21 was dissolved in 10 ml of dimethylformamide in an argon atmosphere, and 350 mg (0.30 mmol) of tetrakistriphenylphosphinepalladium and 2.30 g (10.0 mmol) of silver oxide were added thereto, followed by stirring the mixture at 100° C. for 10 minutes. To the reaction solution was added 5.80 g (15.0 mmol) of (2-fluorophenyl) tributyltin dissolved in 2 ml of dimethylformamide, and the mixture was stirred at 120° C. for 4 hours. The reaction solution was cooled to room temperature, and ethyl acetate and a 2M-ammonium fluoride aqueous solution were added thereto. The mixture was stirred at room temperature for 1 hour. The precipitate was filtered through Celite, and the filtrate was extracted with ethyl acetate. The organic layer was washed with a saturated sodium chloride aqueous solution, and dried over anhydrous magnesium sulfate. The resulting product was purified by silica-gel column chromatography (eluent: a mixture of 10% ethyl acetate and hexane) to obtain 1.07 g of the above-mentioned compound (yield 34%).

NMR (CDCl$_3$) δ (ppm): 8.04–7.99(2H, m), 7.43–7.38 (2H, m), 7.23–7.13(3H, m), 3.68 (3H, s), 3.06 (2H, t, J=7 Hz), 2.45 (2H, t, J=7 Hz), 2.13–2.03 (4H, m) MS (m/e): 318 (M$^+$)

Reference Example 23:

5-[4-Fluoro-3-(2-fluorophenyl)phenyl]valeric acid (compound w):

Compound v (1.50 g, 4.70 mmol) obtained in Reference Example 22 was dissolved in 5 ml of trifluoroacetic acid, and 1.81 ml (11.3 mmol) of triethylsilane was added thereto. After the mixture was heat-reflexed for 1 hour, the solvent was distilled off, and the residue was poured into water, and extracted with chloroform. The organic layer was washed with water, and dried over anhydrous magnesium sulfate. The resulting product was purified by silica-gel column chromatography (eluent: a mixture of 5% ethyl acetate and hexane) to obtain 1.02 g of the above-mentioned compound (yield 73%).

NMR (CDCl$_3$) δ (ppm): 7.40–7.03 (7H, m), 3.66 (3H, s), 2.64 (2H, t, J=7 Hz), 2.34 (2H, t, J=7 Hz), 1.69–1.60 (4H, m) MS (m/e): 304 (M$^+$)

Reference Example 24:

8-Fluoro-7-(2-fluorophenyl)-1-benzsuberone (compound x):

To 1.0 g (3.28 mmol) of compound w obtained in Reference Example 23 was added 20 ml of polyphosphoric acid, and the mixture was stirred at 100° C. for 3 hours. The reaction mixture was poured into 100 ml of water containing ice, and the reaction product was extracted with chloroform. The organic layer was dried over anhydrous magnesium sulfate, and purified by silica-gel column chromatography (eluent: a mixture of 3% ethyl acetate and hexane) to obtain 570 mg of the above-mentioned compound (yield: 64%).

NMR (CDCl$_3$) δ (ppm): 7.55(1H, d, J=10 Hz), 7.43–7.35 (2H, m), 7.26–7.13(3H, m), 2.96(2H, t, J=6 Hz), 2.78(2H, t, J=6 Hz), 1.93–1.82 (4H, m) MS (m/e): 272 (M$^+$)

Reference Example 25:

8-Phenyl-1-benzocyclooctanone (compound y):

Using 2.0 g (7.90 mmol) of 8-bromo-1-benzocyclooctanone and 4.05 g (9.48 mmol) of tetraphenyltin, the same reaction as described in Reference Example 18 was carried out to obtain 1.12 g of the above-mentioned compound (yield 57%).

NMR (CDCl₃) δ (ppm): 7.84(1H, d, J=8 Hz), 7.63–7.34 (7H, m), 3.16(2H, t, J=6 Hz), 2.99(2H, t, J=6 Hz), 1.93–1.80 (4H, m), 1.59–1.50 (2H, m) MS (m/e): 250 (M⁺)

Reference Example 26:

3,4-Dihydro-4-fluoro-6-phenyl-1(2H)-naphthalenone (compound z):

Using 2.00 g (6.41 mmol) of 3,4-dihydro-7-fluoro-6-trifluoromethylsulfonyloxy-1(2H)-naphthalenone and 2.74 g (6.41 mmol) of tetraphenyltin, the same reaction as described in Reference Example 1 was carried out to obtain 1.13 g of the above-mentioned compound (yield 73%).

NMR (CDCl₃) δ (ppm): 7.79(1H, d, J=11 Hz), 7.59–7.32 (6H, m), 2.98(2H, t, J=6 Hz), 2.68(2H, t, J=6 Hz), 2.22–2.15 (2H, m) MS (m/e): 240 (M⁺)

Reference Example 27:

3,4-Dihydro-7-fluoro-6-(2-fluorophenyl)-1(2H)-naphthalenone (compound aa):

Using 1.50 g (4.80 mmol) of 3,4-dihydro-7-fluoro-6-trifluoromethylsulfonyloxy-1(2H)-naphthalenone and 2.22 g (5.78 mmol) of 2-fluorophenyltributyltin, the same reaction as described in Reference Example 1 was carried out to obtain 0.66 g of the above-mentioned compound (yield 53%).

NMR (CDCl₃) δ (ppm): 7.79(1H, d, J=11 Hz), 7.45–7.12 (5H, m), 2.98(2H, t, J=6 Hz), 2.68(2H, t, J=6 Hz), 2.22–2.15 (2H, m)

Reference Example 28:

3,4-Dihydro-7-fluoro-6-(4-fluorophenyl)-1(2H)-naphthalenone (compound bb):

Using 1.50 g (4.80 mmol) of 3,4-dihydro-7-fluoro-6-trifluoromethylsulfonyloxy-1(2H)-naphthalenone and 1.85 g (4.80 mmol) of 4-fluorophenyltributyltin, the same reaction as described in Reference Example 1 was carried out to obtain 0.76 g of the above-mentioned compound (yield 61%).

NMR (CDCl₃) δ (ppm): 7.78(1H, d, J=11 Hz), 7.57–7.50 (2H, m), 7.30(1H, d, J=7 Hz), 7.15 (2H, t, J=9 Hz), 2.98 (2H, t, J=6 Hz), 2.68(2H, t, J=6 Hz), 2.22–2.15(2H, m)

Reference Example 29:

7-(4-Fluorophenyl)-1-benzsuberone (compound cc):

Using 2.50 g (10.46 mmol) of 7-bromo-1-benzsuberone and 5.93 g (15.4 mmol) of (4-fluorophenyl)tributyltin, the same reaction as described in Reference Example 18 was carried out to obtain 1.41 g of the above-mentioned compound (yield 53%).

NMR (CDCl₃) δ (ppm): 7.81(1H, d, J=8 Hz), 7.61–7.11 (6H, m), 3.00(2H, t, J=6 Hz), 2.77(2H, t, J=6 Hz), 1.95–1.81 (4H, m)

Reference Example 30:

7-(3-Fluorophenyl)-1-benzsuberone (compound dd):

Using 2.0 g (7.93 mmol) of 7-bromo-1-benzsuberone and 4.29 g (11.1 mmol) of (3-fluorophenyl) tributyltin, the same reaction as described in Reference Example 18 was carried out to obtain 1.26 g of the above-mentioned compound (yield 63%).

NMR (CDCl₃) δ (ppm): 7.82(1H, d, J=8 Hz), 7.52–7.03 (6H, m), 3.01(2H, t, J=7 Hz), 2.77(2H, t, J=7 Hz), 1.95–1.83 (4H, m)

Reference Example 31:

7-(2,4-Difluorophenyl)-1-benzsuberone (compound ee):

Using 2.0 g (7.93 mmol) of 7-bromo-1-benzsuberone and 4.81 g (11.9 mmol) of (2,4-difluorophenyl)tributyltin, the same reaction as described in Reference Example 18 was carried out to obtain 1.79 g of the above-mentioned compound (yield 83%).

NMR (CDCl₃) δ (ppm): 7.82(1H, d, J=8 Hz), 7.43–7.30 (3H, m), 7.03–6.98(2H, m), 2.99(2H, t, J=6 Hz), 2.78(2H, t, J=6 Hz), 1.94–1.85 (4H, m)

Reference Example 32:

7-(4-Methoxyphenyl)-1-benzsuberone (compound ff):

Using 4.3 g (17.1 mmol) of 7-bromo-1-benzsuberone and 8.85 g (22.2 mmol) of (4-methoxyphenyl)tributyltin, the same reaction as described in Reference Example 18 was carried out to obtain 3.38 g of the above-mentioned compound (yield 74%).

NMR (CDCl₃) δ (ppm): 7.81(1H, d, J=8 Hz), 7.59–7.39 (4H, m), 6.99(2H, d, J=8 Hz), 3.86(3H, s), 3.00(2H, t, J=6 Hz), 2.76(2H, t, J=6 Hz), 1.95–1.82(4H, m)

Reference Example 33:

7-(4-Hydroxyphenyl)-1-benzsuberone (compound gg):

Compound ff (1.6 g, 6.0 mmol) obtained in Reference Example 32 was dissolved in 30 ml of toluene, and 1.6 g (12.0 mmol) of aluminum trichloride was added thereto, followed by heat-refluxing the mixture for 2 hours. The reaction solution was cooled to room temperature, and poured into 2N-hydrochloric acid, and extracted with ether. The organic layer was dried over anhydrous magnesium sulfate and purified by silica-gel column chromatography (eluent: a mixture of 25% ethyl acetate and hexane) to obtain 1.32 g of the above-mentioned compound (yield 87%).

NMR (CDCl₃) δ (ppm): 7.81(1H, d, J=8 Hz), 7.54–7.37 (4H, m), 6.97–6.92(2H, m), 5.65(1H, s), 2.99(2H, t, J=6 Hz), 2.78(2H, t, J=6 Hz), 1.94–1.81(4H, m)

Reference Example 34:

7-(2-Methoxyphenyl)-1-benzsuberone (compound hh):

Using 4.5 g (17.9 mmol) of 7-bromo-1-benzsuberone and 10.7 g (26.9 mmol) of (2-methoxyphenyl)tributyltin, the same reaction as described in Reference Example 18 was carried out to obtain 2.14 g of the above-mentioned compound (yield 45%).

NMR (CDCl₃) δ (ppm): 7.78(1H, d, J=8 Hz), 7.52–7.21 (4H, m), 7.06–6.98(2H, m), 3.82(3H, s), 2.99(2H, t, J=6 Hz), 2.76(2H, t, J=6 Hz) , 1.91–1.82(4H, m)

Reference Example 35:

7-(2-Hydroxyphenyl)-1-benzsuberone (compound ii):

Using 1.81 g (6.8 mmol) of 7-(2-methoxyphenyl)-1-benzsuberone, the same reaction as described in Reference Example 33 was carried out to obtain 0.94 g of the above-mentioned compound (yield 55%).

NMR (CDCl$_3$) δ (ppm): 7.84(1H, d, J=8 Hz), 7.40–7.25 (4H, m), 7.04–6.96(2H, m), 5.34(1H, s), 2.99(2H, t, J=6 Hz), 2.78(2H, t, J=6 Hz), 1.95–1.84(4H, m)

Reference Example 36:

7-(2-Thienyl)-1-benzsuberone (compound jj):

Using 3.0 g (12.6 mmol) of 7-bromo-1-benzsuberone and 6.56 g (17.6 mmol) of (2-thienyl)tributyltin, the same reaction as described in Reference Example 18 was carried out to obtain 1.80 g of the above-mentioned compound (yield 60%).

NMR (CDCl$_3$) δ (ppm): 7.77(1H, d, J=8 Hz), 7.56–7.08 (5H, m), 2.97(2H, t, J=6 Hz), 2.75(2H, t, J=6 Hz), 1.93–1.77 (4H, m)

Reference Example 37:

7-(2-Pyridyl)-1-benzsuberone (compound kk):

Using 3.0 g (12.6 mmol) of 7-bromo-1-benzsuberone and 6.46 g (17.6 mmol) of (2-pyridyl)tributyltin, the same reaction as described in Reference Example 18 was carried out to obtain 1.86 g of the above-mentioned compound (yield 64%).

NMR (CDCl$_3$) δ (ppm): 8.73–8.71(1H, m), 7.91–7.76 (5H, m), 7.29–7.24(1H, m), 3.04 (2H, t, J=6 Hz), 2.77 (2H, t, J=6 Hz), 1.95–1.82 (4H, m)

Reference Example 38:

8-Fluoro-7-phenyl-1-benzsuberone (compound LL):

Using 4.0 g (13.2 mmol) of compound u obtained in Reference Example 21 and 8.46 g (19.8 mmol) of tetraphenyltin, the same reaction as described in Reference Examples 22, 23 and 24 was carried out to obtain 1.36 g of the above-mentioned compound (yield 44%).

NMR (CDCl$_3$) δ (ppm): 7.56–7.24(7H, m), 2.94(2H, t, J=6 Hz), 2.75(2H, t, J=6 Hz), 1.91–1.81(4H, m)

EXAMPLE 39:

8-Fluoro-7-(4-fluorophenyl)-1-benzsuberone (compound mm):

Using 5.0 g (16.7 mmol) of compound u obtained in Reference Example 21 and 8.4 g (21.66 mmol) of (4-fluorophenyl)tributyltin, the same reaction as described in Reference Example 38 was carried out to obtain 1.71 g of the above-mentioned compound (yield 39%).

NMR (CDCl$_3$) δ (ppm): 7.57–7.51(3H, m), 7.26–7.11 (3H, m), 2.96(2H, t, J=6 Hz), 2.77(2H, t, J=6 Hz), 1.93–1.81 (4H, m)

Reference Example 40:

Methyl 4-(3-bromo-4-methoxybenzoyl)butyrate (compound nn):

Using 25 g (134 mmol) of 2-bromoanisole, the same reaction as described in Reference Example 21 was carried out to obtain 37.5 g of the above-mentioned compound (yield 89%).

NMR (CDCl$_3$) δ (ppm): 8.17 (1H, d, J=2 Hz), 7.93 (1H, dd, J=9 Hz, 2 Hz), 6.93(1H, d, J=9 Hz), 3.97(3H, s), 3.69(3H, s), 2.99(2H, t, J=7 Hz), 2.44(2H, t, J=7 Hz), 2.11–2.00(2H, m)

Reference Example 41:

8-Methoxy-7-phenyl-1-benzsuberone (compound oo):

Using 6.0 g (19.8 mmol) of compound nn obtained in Reference Example 40 and 16.3 g (38.0 mmol) of tetraphenyltin, the same reaction as described in Reference Example 38 was carried out to obtain 2.95 g of the above-mentioned compound (yield 44%).

NMR (CDCl$_3$) δ (ppm): 7.81–7.01(7H, m), 3.82(3H, s), 2.99(2H, t, J=6 Hz), 2.77 (2H, t, J=6 Hz), 1.94–1.83 (4H, m)

Reference Example 42:

7-(2-Fluorophenyl)-8-methoxy-1-benzsuberone (compound pp):

Using 5.0 g (15.9 mmol) of compound nn obtained in Reference Example 40 and 8.0 g (20.6 mmol) of (2-fluorophenyl)tributyltin, the same reaction as described in Reference Example 38 was conducted to obtain 1.48 g of the above-mentioned compound (yield 34%).

NMR (CDCl$_3$) δ (ppm): 7.40–7.09(6H, m), 3.84(3H, s), 2.93(2H, t, J=6 Hz), 2.78 (2H, t, J=6 Hz), 1.91–1.84 (4H, m)

Reference Example 43:

8-Hydroxy-7-phenyl-1-benzsuberone (compound qq):

Using 1.34 g (5.03 mmol) of compound oo obtained in Reference Example 41, the same reaction as described in Reference Example 33 was carried out to obtain 0.91 g of the above-mentioned compound (yield 72%).

NMR (CDCl$_3$) δ (ppm): 7.50–7.37(6H, m), 7.11(1H, s), 5.46(1H, s), 2.91(2H, t, J=6 Hz), 2.76(2H, t, J=6 Hz), 1.90–1.80(4H, m)

Reference Example 44:

Methyl 4-(4-chlorobenzoyl)butyrate (compound rr):

Chlorobenzene (8.13 ml, 79.9 mmol) was dissolved in 100 ml of 1,2-dichloroethane, and 21.3 g (160 mmol) of aluminum trichloride and 12.15 ml (87.9 mmol) of methyl 4-(chloroformyl)butyrate were added thereto, followed by stirring the mixture at room temperature overnight. The reaction solution was poured into hydrochloric acid, and extracted with chloroform. The organic layer was dried over anhydrous magnesium sulfate, and the solvent was then distilled off under reduced pressure. The resulting residue was purified by silica-gel column chromatography (eluent: a mixture of 4% ethyl acetate and hexane) to obtain 15.8 g of the above-mentioned compound (yield 82%).

NMR (CDCl$_3$) δ (ppm): 7.91(2H, d, J=8 Hz), 7.43(2H, d, J=8 Hz), 3.69(3H, s), 3.03(2H, t, J=7 Hz), 2.45(2H, t, J=7 Hz), 2.14–2.01(2H, m)

Reference Example 45:

Methyl 4-(3-bromo-4-chlorobenzoyl)butyrate (compound ss):

Compound rr (15.73 g, 65.5 mmol) obtained in Reference Example 44 was dissolved in 70 ml of 1,2-dichloroethane, and 21.85 g (164 mmol) of aluminum trichloride was added thereto, followed by heat-refluxing the mixture for 20 minutes. The reaction solution was cooled to room temperature, and 5.06 ml (98.3 mmol) of bromine was added thereto. The mixture was heat-refluxed for 6 hours. The reaction solution was cooled to room temperature, and 200 ml of hydrochloric acid was added thereto. The mixture was filtered through Celite. The filtrate was extracted with chloroform. The organic layer was dried over anhydrous magnesium sulfate, and the solvent was then distilled off under reduced pressure. The obtained residue was purified by silica-gel column chromatography (eluent: a mixture of 4% ethyl acetate and hexane) to obtain 15.5 g of the above-mentioned compound (yield 74%).

NMR (CDCl$_3$) δ (ppm): 8.20(1H, d, J=2 Hz), 7.83(1H, dd, J=9 Hz, 2 Hz), 7.54(1H, d, J=9 Hz), 3.96(3H, s), 3.02(2H, t, J=7 Hz), 2.45(2H, t, J=7 Hz), 2.14–2.01(2H, m)

Reference Example 46:

8-Chloro-7-phenyl-1-benzsuberone (compound tt):

Using 5.0 g (15.67 mmol) of compound ss obtained in Reference Example 45 and 9.37 g (21.9 mmol) of tetraphenyltin, the same reaction as described in Reference Example 38 was carried out to obtain 3.35 g of the above-mentioned compound (yield 68%).

NMR (CDCl$_3$) δ (ppm): 7.85(1H, s), 7.50–7.20(6H, m), 2.94(2H, t, J=6 Hz), 2.77 (2H, t, J=6 Hz), 1.96–1.82 (4H, m)

Reference Example 47:

1-[(2-Fluoro-3-phenyl)phenyl]cyclopentanol (compound uu):

5.00 g (29.0 mmol) of 2-fluorobiphenyl was dissolved in 50 ml of tetrahydrofuran, and 5.0 ml (33.1 mmol) of tetramethylethylenediamine was added thereto. While cooling the solution to –78° C., 32 ml (32 mmol) of sec-butyllithium was added thereto, and the mixture was stirred for 4 hours. Then, 3.0 ml (33.9 mmol) of cyclopentanone was dissolved in 2 ml of tetrahydrofuran, and the solution was gradually added at –78° C. The mixture was further stirred for 30 minutes. The reaction mixture was poured into an ammonium chloride aqueous solution, and extracted with ether. The organic layer was washed with a saturated sodium chloride aqueous solution, and dried over anhydrous magnesium sulfate. After the solvent was distilled off under reduced pressure, the residue was purified by silica-gel column chromatography (eluent: a mixture of 5% ethyl acetate and hexane) to obtain 5.40 g of the above-mentioned compound (yield 73%).

NMR (CDCl$_3$) δ (ppm): 7.57–7.09(8H, m), 2.72(1H, brs), 2.17–1.80(8H, m)

Reference Example 48:

4-[2-Fluoro-3-phenyl)benzoyl]butanoic acid (compound vv):

Compound uu (3.85 g, 15.0 mmol) obtained in Reference Example 47 was dissolved in 100 ml of acetic acid, and 8.0 g (80 mmol) of chromic anhydride was carefully added thereto in several divided portions, followed by stirring the mixture at room temperature for 3 hours. The reaction mixture was poured into a sodium sulfite aqueous solution, and extracted with ether to obtain 3.00 g of the above-mentioned compound (yield 70%).

NMR (CDCl$_3$) δ (ppm): 7.84–7.78(1H, m), 7.61–7.26 (7H, m), 3.14–3.07(2H, m), 2.48(2H, t, J=7 Hz), 2.14–2.03 (2H, m)

Reference Example 49:

5-[(2-Fluoro-3-phenyl) benzoyl]pentanoic acid (compound ww):

Using 3.0 g (10.5 mmol) of compound vv obtained in Reference Example 48, the same reaction as that described in Reference Example 11 was carried out to obtain 2.0 g of the above-mentioned compound (yield 70%).

NMR (CDCl$_3$) δ (ppm): 7.55–7.07(8H, m), 2.72(2H, t, J=6 Hz), 2.40(2H, t, J=6 Hz), 1.80–1.60 (4H, m)

Reference Example 50:

6-Fluoro-7-phenyl-1-benzsuberone (compound xx):

Using 2.0 g (7.3 mmol) of compound ww obtained in Reference Example 49, the same reaction as described in Reference Example 12 was carried out to obtain 1.60 g of the above-mentioned compound (yield 86%).

NMR (CDCl$_3$) δ (ppm): 7.58–7.31(7H, m), 3.03(2H, t, J=6 Hz), 2.75(2H, t, J=6 Hz), 1.95–1.79(4H, m)

Reference Example 51:

1-[(3-Fluoro-5-phenyl)phenyl]cyclopentanol (compound yy):

Using 10.0 g (39.8 mmol) of 1-bromo-3-fluoro-5-phenylbenzene, the same reaction as described in Reference Example 47 was carried out to obtain 8.06 g of the above-mentioned compound (yield 79%).

NMR (CDCl$_3$) δ (ppm): 7.62–7.09(8H, m), 2.06–1.85 (8H, m)

Reference Example 52:

4-[(3-Fluoro-5-phenyl)benzoyl]butanoic acid (compound zz):

Using 2.57 g (10.0 mmol) of compound yy obtained in Reference Example 51, the same reaction as described in Reference Example 48 was carried out to obtain 2.09 g of the above-mentioned compound (yield 73%).

NMR (CDCl$_3$) δ (ppm): 7.97–7.96(1H, m), 7.62–7.38 (7H, m), 3.11(2H, t, J=7 Hz), 2.53(2H, t, J=7 Hz), 2.16–2.06 (2H, m)

EXAMPLE 53:

5-[3-Fluoro-5-phenyl) benzoyl]pentanoic acid (compound aaa):

Compound zz (3.0 g, 11.2 mmol) obtained in Reference Example 52 was dissolved in 50 ml of diethylene glycol, and 2.0 g of potassium hydroxide and 1.5 ml (31 mmol) of hydrazine monohydrate were added to the solution. The mixture was stirred at 120° C. for 2 hours and further stirred at 190° C. for 5 hours. After cooling, the reaction mixture was poured into hydrochloric acid, and extracted with ether to obtain 2.4 g of the above-mentioned compound (yield 84%).

NMR (CDCl$_3$) δ (ppm): 7.55–7.08(8H, m), 2.73(2H, t, J=6 Hz), 2.40(2H, t, J=6 Hz), 1.75–1.65(4H, m)

Reference Example 54:

9-Fluoro-7-phenyl-1-benzsuberone (compound bbb):

Using 2.4 g (8.8 mmol) of compound aaa obtained in Reference Example 53, the same reaction as described in Reference Example 12 was carried out to obtain 1.60 g of the above-mentioned compound (yield 71%).

NMR (CDCl$_3$) δ (ppm): 7.60–7.18(7H, m), 2.89(2H, t, J=6 Hz), 2.70(2H, t, J=6 Hz), 1.92–1.81 (4H, m)

Reference Example 55:

1-[2-Methoxy-3-phenyl)phenyl]cyclopentanol (compound ccc):

Using 19.0 g (103 mmol) of 2-methoxybiphenyl, the same reaction as described in Reference Example 47 was carried out to obtain 8.8 g of the above-mentioned compound (yield 32%).

NMR (CDCl$_3$) δ (ppm): 7.58–7.08(8H, m), 3.39(1H, s), 3.38(3H, s), 2.12–1.77 (8H, m)

Reference Example 56:

4-[(2-Methoxy-3-phenyl) benzoyl]butanoic acid (compound ddd):

Using 8.8 g (32.8 mmol) of compound ccc obtained in Reference Example 55, the same reaction as described in Reference Example 48 was carried out to obtain 2.87 g of the above-mentioned compound (yield 29%).

NMR (CDCl$_3$) δ (ppm): 7.57–7.18 (8H, m), 3.38(3H, s), 3.11(2H, t, J=7 Hz), 2.49(2H, t, J=7 Hz), 2.12–2.04(2H, m)

Reference Example 57:

5-[(2-Methoxy-3-phenyl)benzoyl]pentanoic acid (compound eee):

Using 2.87 g (9.62 mmol) of compound ddd obtained in Reference Example 56, the same reaction as described in Reference Example 11 was carried out to obtain 2.54 g of the above-mentioned compound (yield 93%).

NMR (CDCl$_3$) δ (ppm): 7.58–7.06(8H, m), 3.33(3H, s), 2.71(2H, t, J=6 Hz), 2.42(2H, t, J=6 Hz), 1.82–1.70(4H, m)

Reference Example 58:

6-Methoxy-7-phenyl-1-benzsuberone (compound fff):

Using 1.75 g (6.16 mmol) of compound eee obtained in Reference Example 57, the same reaction as described in Reference Example 12 was carried out to obtain 0.50 g of the above-mentioned compound (yield 31%).

NMR (CDCl$_3$) δ (ppm): 7.61–7.22(7H, m), 3.36(3H, s), 3.06(2H, t, J=6 Hz), 2.77(2H, t, J=6 Hz), 1.93–1.81(4H, m)

Reference Example 59:

1-[(2,6-Difluoro-3-phenyl)phenyl]cyclopentanol (compound ggg):

Using 10.6 g (55.7 mmol) of 2,6-difluorobiphenyl, the same reaction as described in Reference Example 47 was carried out to obtain 10.5 g of the above-mentioned compound (yield 69%).

NMR (CDCl$_3$) δ (ppm): 7.52–7.33(6H, m), 6.94–6.87 (1H, m), 2.16–1.74(8H, m)

Reference Example 60:

4-[(2,6-Difluoro-3-phenyl)benzoyl]butanoic acid (compound hhh):

Using 10.4 g (37.9 mmol) of compound ggg obtained in Reference Example 59, the same reaction as described in Reference Example 48 was carried out to obtain 7.31 g of the above-mentioned compound (yield 63%).

NMR (CDCl$_3$) δ (ppm): 7.94–7.88(1H, m), 7.94–7.44 (5H, m), 7.06–7.02(1H, m), 3.10–3.03(2H, m), 2.47(2H, t, J=7 Hz), 2.12–2.04(2H, m)

Reference Example 61:

5-[(2,6-Difluoro-3-phenyl)benzoyl]pentanoic acid (compound iii):

Compound hhh (3.60 g, 11.8 mmol) obtained in Reference Example 60 was dissolved in 40 ml of dichloromethane, and 1.22 ml (14.2 mmol) of ethanedithiol and 1.5 ml of a boron trifluoride ether complex were added thereto. The solution was stirred at room temperature for 24 hours. The mixture was extracted with water, dissolved in 50 ml of ethanol, 5 g of Raney nickel (made by Aldrich) was added thereto, and the mixture was heat-refluxed for 30 minutes. The reaction mixture was filtered through Celite, and the solvent was distilled off to obtain 1.74 g of the above-mentioned compound (yield 51%).

NMR (CDCl$_3$) δ (ppm): 7.46–7.34(5H, m), 7.15–7.07 (1H, m), 6.93–6.86(1H, m), 2.67(2, t, J=6 Hz), 2.39(2H, t, J=6 Hz), 1.75–1.67(4H, m)

Reference Example 62:

6,8-Difluoro-7-phenyl-1-benzsuberone (compound jjj):

Using 1.4 g (4.8 mmol) of compound iii obtained in Reference Example 61, the same reaction as described in Reference Example 12 was carried out to obtain 0.6 g of the above-mentioned compound (yield 46%).

NMR (CDCl$_3$) δ (ppm): 7.48–7.35(6H, m), 3.00(2H, t, J=6 Hz), 2.78(2H, t, J=6 Hz), 1.93–1.84(4H, m)

Reference Example 63:

7-Phenyl-1-benzsuberone (compound kkk):

Using 4.0 g (15.8 mmol) of 7-bromo-1-benzsuberone and 8.14 g (19.0 mmol) of tetraphenyltin, the same reaction as described in Reference Example 18 was carried out to obtain 3.07 g of the above-mentioned compound (yield 77%).

NMR (CDCl$_3$) δ (ppm): 7.83(1H, d, J=8 Hz), 7.63–7.37 (7H, m), 3.00(2H, t, J=6 Hz), 2.77(2H, t, J=6 Hz), 1.95–1.83 (4H, m)

Reference Example 64:

7-Phenyl-1-benzsuberol (compound LLL):

Compound kkk (1.83 g, 7.75 mmol) obtained in Reference Example 63 was dissolved in 20 ml of methanol, and 0.30 g (7.93 mmol) of sodium borohydride was added thereto, followed by stirring the solution at room temperature for 1 hour. After the solvent was removed, the residue was poured into water, and extracted with ethyl acetate to obtain 1.84 g of the above-mentioned compound (yield 100%).

NMR (CDCl$_3$) δ (ppm): 7.61–7.29(8H, m), 4.97(1H, d, J=7 Hz), 2.99(1H, dd, J=7 Hz, J=13 Hz), 2.82–2.73(1H, m), 2.12–1.47(6H, m)

Reference Example 65:

9-Methyl-7-phenyl-1-benzsuberol (compound mmm):

Compound LLL (2.15 g, 9.02 mmol) obtained in Reference Example 64 was dissolved in 30 ml of heptane, and 3.0 ml (19.9 mmol) of tetramethylethylenediamine and 12.4 ml (19.8 mmol) of n-butyllithium were added thereto, followed by heat-refluxing the mixture for 2 hours. The reaction mixture was cooled to room temperature, and 1,2 ml (19.2 mmol) of methyllithium was added thereto. The mixture was further stirred for 30 minutes. The reaction mixture was poured into an ammonium chloride aqueous solution, and extracted with ether. The organic layer was washed with a saturated sodium chloride aqueous solution, and with dried over magnesium anhydride. After the solvent was distilled off under reduced pressure, the residue was purified by silica-gel column chromatography (eluent: a mixture of 5% ethyl acetate and hexane) to obtain 0.50 g of the above-mentioned compound (yield 22%).

NMR (CDCl$_3$) δ (ppm): 7.59–7.18(7H, m), 5.38(1H, d, J=6 Hz), 3.43–3.33(1H, m), 2.72–2.65(1H, m), 2.42(3H, s), 2.27–1.38(6H, m)

Reference Example 66:

9-Methyl-7-phenyl-1-benzsuberone (compound nnn):

Compound mmm (0.29 g, 1.15 mmol) obtained in Reference Example 65 was dissolved in 5 ml of dichloromethane, and 0.50 g (2.32 mmol) of pyridinium chroromate was added thereto, followed by stirring the mixture at room temperature for 1 hour. The reaction mixture was purified by silica-gel column chromatography (eluent: dichloromethane) to obtain 0.27 g of the above-mentioned compound (yield 94%).

NMR (CDCl$_3$) δ (ppm): 7.62–7.15(7H, m), 2.82(1H, d, J=6 Hz), 2.62(2H, t, J=6 Hz), 2.38(3H, s), 1.86–1.77(4H, m)

Reference Example 67:

Methyl 4-[3-(1-adamantyl)benzoyl]butyrate (compound ooo):

5.0 g (26.0 mmol) of 4-benzoylbutyric acid was dissolved in 100 ml of 1,2-dichloroethane, and 8.70 g (65.03 mmol) of aluminum trichloride and 5.30 (31.21 mmol) of 1-chloroadamantane were added thereto, followed by stirring the mixture at 60° C. for 6 hours. The reaction mixture was poured into hydrochloric acid, and extracted with chloroform. The organic layer was dried over anhydrous magnesium sulfate, and the solvent was then distilled off under reduced pressure. To the residue were added 100 ml of methanol and 5 ml of conc. sulfuric acid, and the mixture was stirred at room temperature overnight. The solvent was distilled off under reduced pressure, and the residue was poured into water, and extracted with chloroform. The organic layer was dried over anhydrous magnesium sulfate, and the solvent was then distilled off under reduced pressure. The resulting residue was purified by silica-gel column chromatography (eluent: a mixture of 1% ethyl acetate and hexane) to obtain 2.13 g of the above-mentioned compound (yield 24%).

NMR (CDCl$_3$) δ (ppm): 7.98–7.20(4H, m), 3.68(3H, s), 3.06(2H, t, J=7 Hz), 2.46(2H, t, J=7 Hz), 2.17–1.64(17H, m)

Reference Example 68:

7-(1-Adamantyl)-1-benzsuberone (compound ppp):

Using 3.44 g (10.12 mmol) of compound ooo obtained in Reference Example 67, the same reaction as described in Reference Examples 23 and 24 was carried out to obtain 0.65 g of the above-mentioned compound (yield 22%).

NMR (CDCl$_3$) δ (ppm): 7.20(1H, d, J=7 Hz), 7.44–7.17 (2H, m), 2.93(2H, t, J=6 Hz), 2.73(2H, t, J=5 Hz), 2.17–1.76 (19H, m)

Industrial Applicability:

The novel tetracyclic compound of this invention is available in the field of medicines such as an immunosuppressive agent and as an agent for treating autoimmune disease.

We claim:

1. A novel tetracyclic compound represented by formula (I)

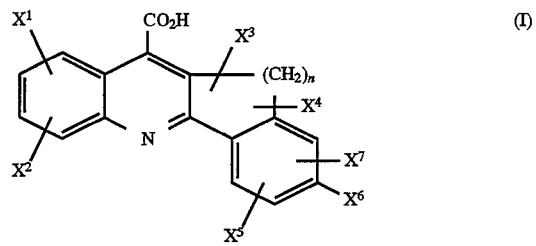

or its pharmacologically acceptable salt, wherein $X^1$ and $X^2$ are the same or different and each represents hydrogen, a lower alkyl, halogen, nitro, hydroxy or a lower alkoxy, $X^3$ and $X^4$ are the same or different and each represents hydrogen or a lower alkyl, $X^5$ and $X^7$ are the same or different and each represents hydrogen, a lower alkyl, halogen, hydroxy or a lower alkoxy, $X^6$ represents a substituted or unsubstituted aryl, a substituted or unsubstituted aromatic heterocyclic group, cycloalkyl, bicycloalkyl or tricycloalkyl, and n is an integer of 1 to 4; provided that when n is 2, $X^6$ represents a substituted aryl, a substituted or unsubstituted aromatic heterocyclic group, cycloalkyl, bicycloalkyl or tricycloalkyl, or $X^6$ represents an unsubstituted aryl, and at least one of $C^5$ and $X^7$ represents a substituent mentioned above other than hydrogen; and provided that when formula (I) is represented by formula (II),

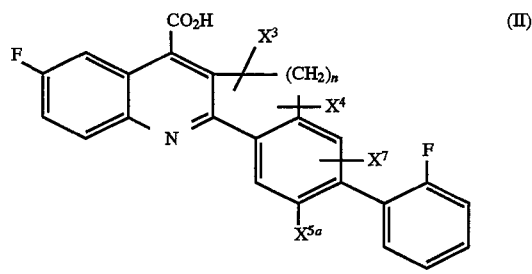

$X^{5a}$ represents a lower alkyl, halogen or a lower alkoxy.

2. The compound or its pharmacologically-acceptable salt of claim 1 wherein $X^1$ and $X^2$ are the same or different and each represents hydrogen or halogen, $X^5$ and $X^7$ are the same or different and each represents hydrogen or halogen, $X^6$ represents a substituted aryl, and n is 2.

3. The compound or its pharmacologically-acceptable salt of claim 2 wherein each of $X^3$ and $X^4$ represents hydrogen, and $X^6$ represents a halo-substituted aryl.

4. The compound or its pharmacologically-acceptable salt of claim 1 wherein $X^1$ and $X^2$ are the same or different and each represents hydrogen or halogen, $X^5$ and $X^7$ are the same or different and each represents hydrogen or halogen, X6 represents aryl, and n is 3.

5. A pharmaceutical composition comprising the compound or its pharmacologically-acceptable salt of claim 1 in an amount effective as an active ingredient, and a pharmacologically-acceptable carrier.

* * * * *

UNITED STATES PATENT AND TRADEMARK OFFICE
CERTIFICATE OF CORRECTION

PATENT NO. : 5,646,283

DATED : July 8, 1997

INVENTOR(S): FUMIO SUZUKI ET AL.

It is certified that error appears in the above-identified patent and that said Letters Patent is hereby corrected as shown below:

COLUMN 1

Line 51, "(I)"," should read --(I)"],--.

COLUMN 2

Line 3, "cycloakyl" should read --cycloalkyl--.
   Line 27, "group" should read --groups--.
   Line 34, "group" should read --groups--.

COLUMN 3

Line 22, "$X^1$" should read --$X^5$--.

COLUMN 5

Line 18, "be also" should read --also be--.
   Line 56, "be also" should read --also be--.

UNITED STATES PATENT AND TRADEMARK OFFICE
CERTIFICATE OF CORRECTION

PATENT NO. : 5,646,283

DATED : July 8, 1997

INVENTOR(S): FUMIO SUZUKI ET AL.

It is certified that error appears in the above-identified patent and that said Letters Patent is hereby corrected as shown below:

COLUMN 6

Line 23, "necessary." should read --necessary. ¶--.
    Line 26, "method" (first occurrence) should read
      --methods--.
    Line 28, "method" (first occurrence) should read
      --methods--.
    Line 30, "be also" should read --also be--.

COLUMN 7

Line 27, "be also" should read --also be--.
    Line 28, "process," should read --process--.

COLUMN 8

Line 20, "method" should read --methods--.

COLUMN 9

Line 17, "alky-" should read --alkyl---.
    Line 18, "1phosphonium" should read --phosphonium--.

COLUMN 10

Line 52, "compounds" should read --compound--.

UNITED STATES PATENT AND TRADEMARK OFFICE
CERTIFICATE OF CORRECTION

PATENT NO. : 5,646,283

DATED : July 8, 1997

INVENTOR(S): FUMIO SUZUKI ET AL.

It is certified that error appears in the above-identified patent and that said Letters Patent is hereby corrected as shown below:

COLUMN 12

Line 35, "be also" should read --also be--.

COLUMN 21

Line 36, "pharmacologicalactivities" should read
     --pharmacological activities--.

COLUMN 23

Line 14, "Control" should read --control--.

COLUMN 24

Line 12, "suggests" should read --suggest--.

COLUMN 26

Line 40, "flitration" should read --filtration--.

COLUMN 55

Line 4, "1,2 ml" should read --1.2 ml--.
   Line 9, "with" should read --was--.

UNITED STATES PATENT AND TRADEMARK OFFICE
CERTIFICATE OF CORRECTION

PATENT NO. : 5,646,283

DATED : July 8, 1997

INVENTOR(S) : FUMIO SUZUKI ET AL.

It is certified that error appears in the above-identified patent and that said Letters Patent is hereby corrected as shown below:

<u>COLUMN 56</u>

Line 32, "$C^5$" should read --$X^5$--.

Signed and Sealed this

Twenty-first Day of April, 1998

Attest:

BRUCE LEHMAN

Attesting Officer

Commissioner of Patents and Trademarks